(12) United States Patent
Shelton, IV et al.

(10) Patent No.: US 12,193,670 B1
(45) Date of Patent: Jan. 14, 2025

(54) SURGICAL STAPLE CARTRIDGE COMPRISING REPLACEABLE ELECTRONICS PACKAGE

(71) Applicant: Cilag GmbH International, Zug (CH)

(72) Inventors: Frederick E. Shelton, IV, Hillsboro, OH (US); Shane R. Adams, Lebanon, OH (US); Taylor W. Aronhalt, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,784

(22) Filed: Oct. 13, 2023

(51) Int. Cl.
*A61B 17/072* (2006.01)
*A61B 17/00* (2006.01)

(52) U.S. Cl.
CPC .................. *A61B 17/07207* (2013.01); *A61B 2017/00398* (2013.01); *A61B 2017/07271* (2013.01)

(58) Field of Classification Search
CPC .............................................. A61B 17/07207
See application file for complete search history.

(56) References Cited

U.S. PATENT DOCUMENTS

| | | |
|---|---|---|
| 9,072,535 B2 | 7/2015 | Shelton, IV et al. |
| 9,993,248 B2 | 6/2018 | Shelton, IV et al. |
| 10,135,242 B2 | 11/2018 | Baber et al. |
| 10,548,504 B2 | 2/2020 | Shelton, IV et al. |
| 11,364,029 B2 | 6/2022 | Burbank et al. |
| 2015/0324317 A1 | 11/2015 | Collins et al. |
| 2018/0168625 A1 | 6/2018 | Posada et al. |
| 2018/0250002 A1 | 9/2018 | Eschbach |
| 2019/0200981 A1 | 7/2019 | Harris et al. |
| 2019/0208641 A1* | 7/2019 | Yates .................... H04N 7/183 |

* cited by examiner

*Primary Examiner* — Nathaniel C Chukwurah

(57) ABSTRACT

A surgical stapling end effector comprising a cartridge channel jaw, an anvil jaw, and a surgical staple cartridge positioned within the cartridge channel jaw is disclosed. The surgical staple cartridge comprises a plurality of staples, a cartridge body comprising a plurality of staple cavities, a longitudinal slot, and an outer lateral cartridge wall comprising a recess defined therein. The surgical staple cartridge further comprises an electronics sub-assembly positioned within the recess, wherein the electronics sub-assembly comprises electrical pathways, a printed circuit board removably attached to the outer lateral cartridge wall within the recess, and a wireless transmission coil electrically coupled to the printed circuit board by way of the electrical pathways, wherein the wireless transmission coil is configured to transmit at least one of power or data between the printed circuit board and a corresponding wireless transmission coil of an instrument to which the surgical staple cartridge is attached.

19 Claims, 20 Drawing Sheets

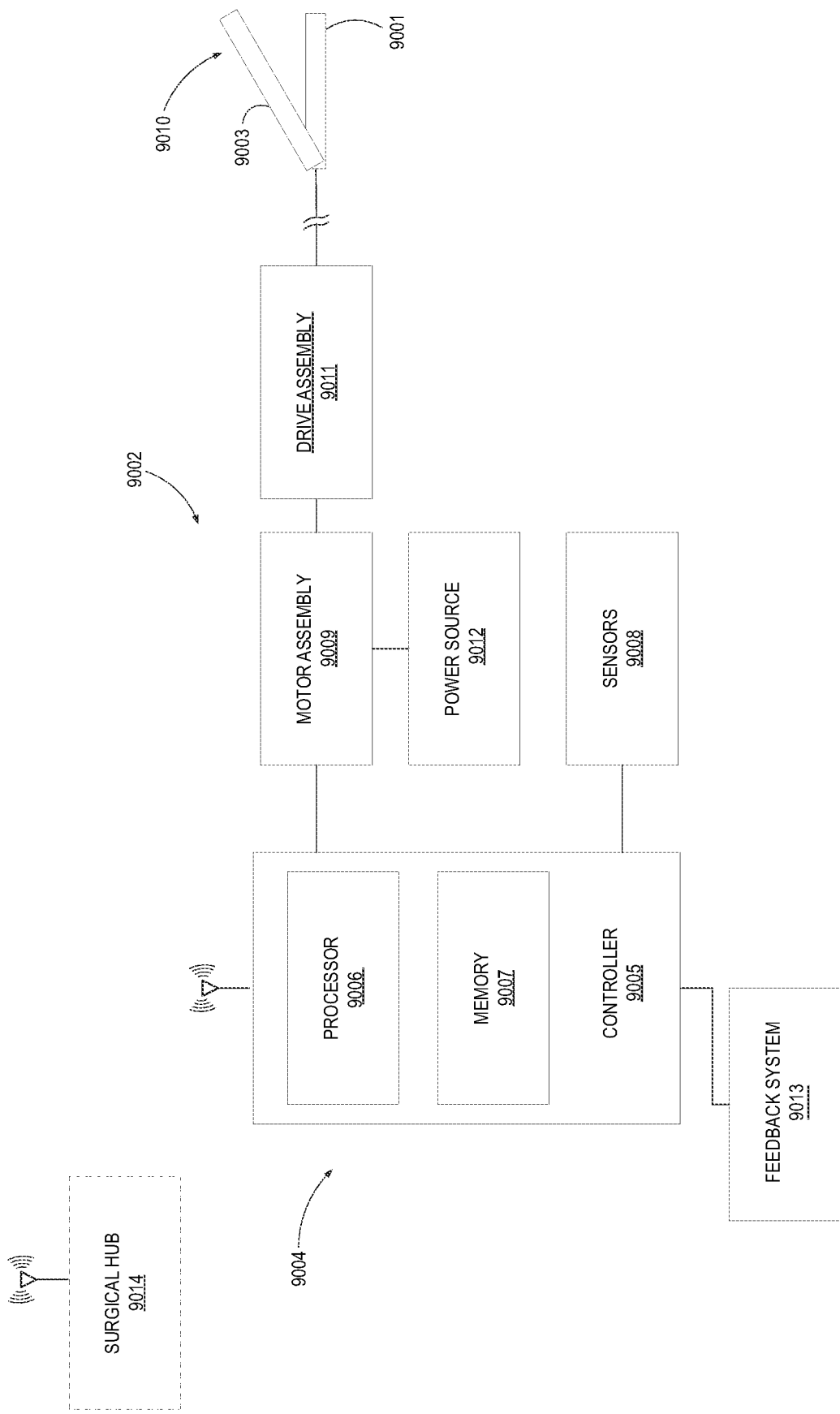

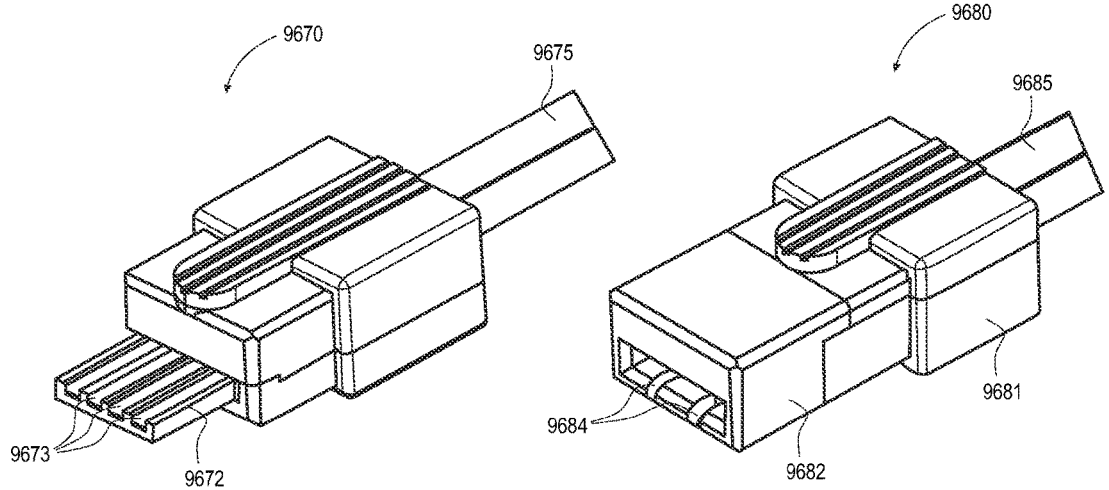
FIG. 15
FIG. 17
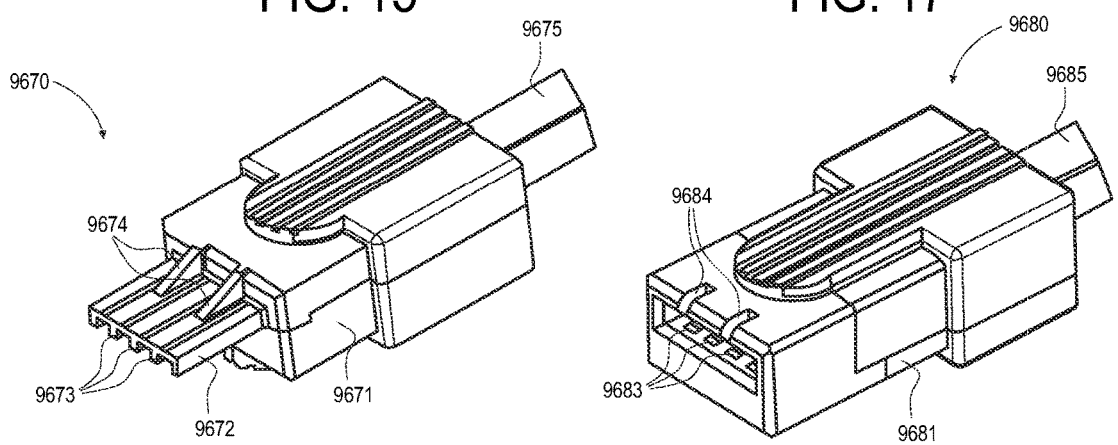
FIG. 16
FIG. 18
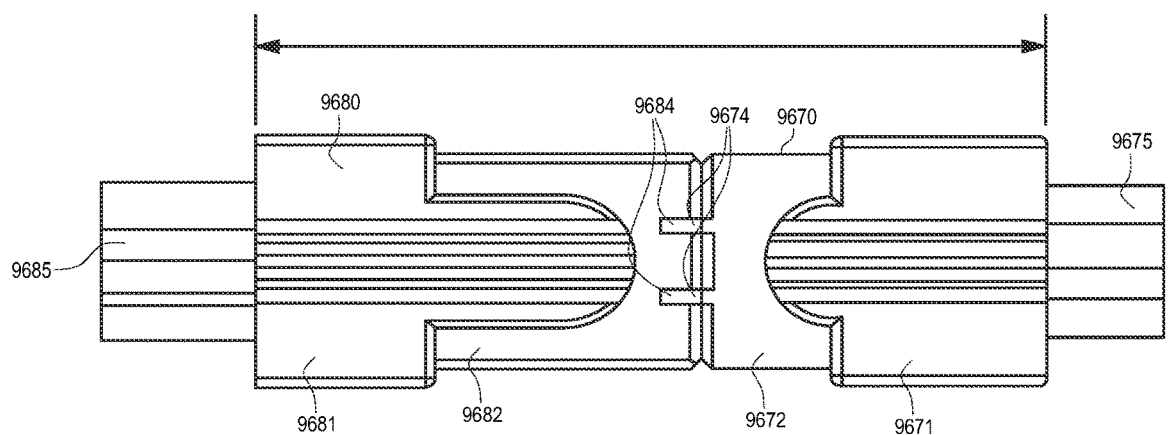
FIG. 19

SURGICAL STAPLE CARTRIDGE COMPRISING REPLACEABLE ELECTRONICS PACKAGE

BACKGROUND

A surgical instrument is utilized in a surgical operating environment. The surgical instrument may be handheld and/or attached to and controlled by a surgical robot. The surgical instrument comprises a surgical stapling instrument configure to clamp, staple, and cut patient tissue during a surgical procedure.

SUMMARY

A surgical stapling end effector comprising a cartridge channel jaw, an anvil jaw, and a surgical staple cartridge positioned within the cartridge channel jaw is disclosed. The surgical staple cartridge comprises a plurality of staples, a cartridge body comprising a plurality of staple cavities, a longitudinal slot, and an outer lateral cartridge wall comprising a recess defined therein. The surgical staple cartridge further comprises an electronics sub-assembly positioned within the recess, wherein the electronics sub-assembly comprises electrical pathways, a printed circuit board removably attached to the outer lateral cartridge wall within the recess, and a wireless transmission coil electrically coupled to the printed circuit board by way of the electrical pathways, wherein the wireless transmission coil is configured to transmit at least one of power or data between the printed circuit board and a corresponding wireless transmission coil of an instrument to which the surgical staple cartridge is attached.

A surgical stapling system comprising a surgical end effector is disclosed. The surgical end effector comprises a first jaw, a second jaw movable relative to the first jaw, a plurality of sensors arranged longitudinally along the surgical end effector, wherein each sensor of the plurality of sensors is configured to sense a parameter of tissue clamped between the first jaw and the second jaw, and wherein the plurality of sensors comprises a first sensor and a plurality of second sensors proximal to the first sensor. The surgical stapling system further comprises a control circuit coupled to the plurality of sensors, wherein the control circuit is configured to monitor an end effector parameter reading of the first sensor, monitor an end effector parameter reading of each sensor of the plurality of second sensors, compare the end effector parameter reading of the first sensor to the end effector parameter readings of the plurality of second sensors, and determine a state of the tissue clamped between the first jaw and the second jaw based on the comparison of the end effector parameter reading of the first sensor and the end effector parameter readings of the plurality of second sensors.

BRIEF DESCRIPTION OF THE DRAWINGS

In the description, for purposes of explanation and not limitation, specific details are set forth, such as particular aspects, procedures, techniques, etc. to provide a thorough understanding of the present technology. However, it will be apparent to one skilled in the art that the present technology may be practiced in other aspects that depart from these specific details.

The accompanying drawings, where like reference numerals refer to identical or functionally similar elements throughout the separate views, together with the detailed description below, are incorporated in and form part of the specification, and serve to further illustrate aspects of concepts that include the claimed disclosure and explain various principles and advantages of those aspects.

FIG. 1 is a block diagram of a surgical system comprising an end effector, a motor-driven drive assembly, and a control circuit configured to control actuation of the motor-driven drive assembly, wherein the control circuit is electrically coupled with electronic circuits of a replaceable staple cartridge of the end effector, in accordance with the present disclosure;

FIG. 15 is a perspective view of an electrical connector in accordance with the present disclosure;

FIG. 16 is a perspective view of the electrical connector of FIG. 15;

FIG. 17 is a perspective view of an electrical connector in accordance with the present disclosure;

FIG. 18 is a perspective view of the electrical connector of FIG. 17;

FIG. 19 is an elevational view of the electrical connectors in a connected configuration of FIGS. 15 and 17;

Corresponding reference characters indicate corresponding parts throughout the several views.

DESCRIPTION

Figure 3:
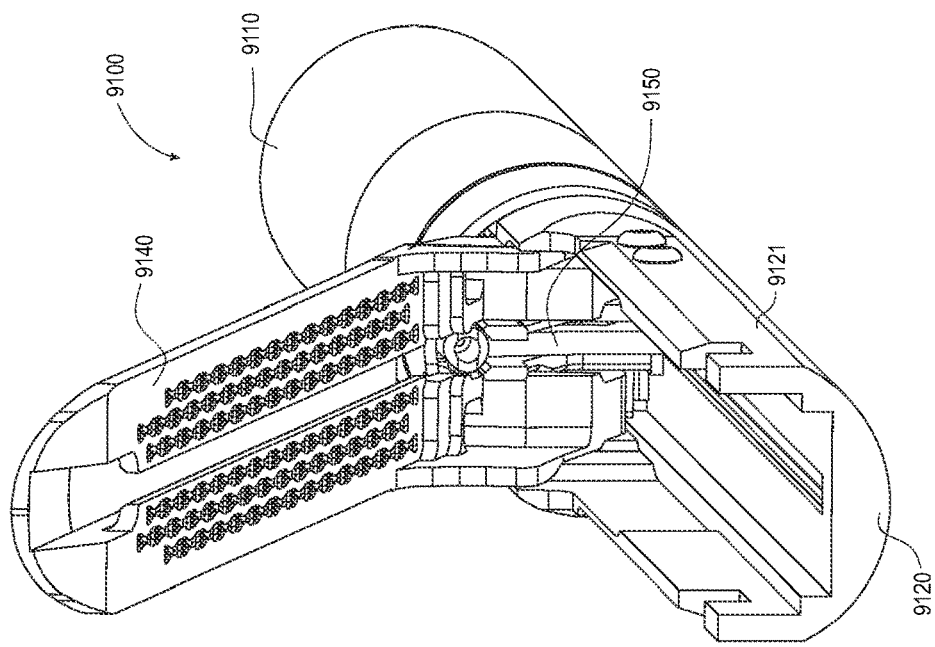
FIG. 3 is a partial perspective view of the surgical stapling end effector of FIG. 2, wherein the surgical stapling assembly comprises a shaft, a first jaw, and a second jaw movable relative to the first jaw to clamp tissue therebetween.

Applicant of the present application owns the following U.S. patent applications that were filed on Oct. 13, 2023 and which are each herein incorporated by reference in their respective entireties:

U.S. patent application Ser. No. 18/379,759, titled METHOD OF OPERATING A SURGICAL STAPLING INSTRUMENT;

U.S. patent application Ser. No. 18/379,762, titled SURGICAL STAPLING SYSTEMS WITH ADAPTIVE STAPLE FIRING ALGORITHMS;

U.S. patent application Ser. No. 18/379,763, titled LEARNED TRIGGERS FOR ADAPTIVE CONTROL OF SURGICAL STAPLING SYSTEMS;

U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;

U.S. patent application Ser. No. 18/379,768, titled PROPORTIONATE BALANCING OF THE FUNCTION IMPACT MAGNITUDE OF BATTERY OUTPUT TO PEAK MOTOR CURRENT;

U.S. patent application Ser. No. 18/379,771, titled MOTOR OPTIMIZATION BY MINIMIZATION OF PARASITIC LOSSES AND TUNING MOTOR DRIVE CONFIGURATION;

U.S. patent application Ser. No. 18/379,773, titled APPARATUS AND METHOD TO REDUCE PARASITIC LOSSES OF THE ELECTRICAL SYSTEM OF A SURGICAL INSTRUMENT;

U.S. patent application Ser. No. 18/379,776, titled SURGICAL TOOL WITH RELAXED FLEX CIRCUIT ARTICULATION;

U.S. patent application Ser. No. 18/379,777, titled WIRING HARNESS FOR SMART STAPLER WITH MULTI AXIS ARTICULATION; and U.S. patent application Ser. No. 18/379,781, titled SURGICAL SYSTEM WITH WIRELESS ARRAY FOR POWER AND DATA TRANSFER.

Applicant of the present application owns the following U.S. patent applications that were filed on Oct. 13, 2023 and which are each herein incorporated by reference in their respective entireties:

U.S. patent application Ser. No. 18,379,790, titled METHOD OF ASSEMBLING A STAPLE CARTRIDGE;

U.S. patent application Ser. No. 18/379,793, titled CONTROL SURFACES ON A STAPLE DRIVER OF A SURGICAL STAPLE CARTRIDGE;

U.S. patent application Ser. No. 18/379,796, titled INTEGRAL CARTRIDGE STIFFENING FEATURES TO REDUCE CARTRIDGE DEFLECTION;

U.S. patent application Ser. No. 18/379,801, titled STAPLE CARTRIDGE COMPRISING WALL STRUCTURES TO REDUCE CARTRIDGE DEFLECTION;

U.S. patent application Ser. No. 18/379,803, titled PANLESS STAPLE CARTRIDGE ASSEMBLY COMPRISING RETENTION FEATURES FOR HOLDING STAPLE DRIVERS AND SLED;

U.S. patent application Ser. No. 18/379,805, titled STAPLE CARTRIDGE COMPRISING A SLED HAVING A DRIVER LIFT CAM;

U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;

U.S. patent application Ser. No. 18/379,810, titled STAPLE CARTRIDGE COMPRISING A COMPOSITE SLED;

U.S. patent application Ser. No. 18/379,811, titled SURGICAL INSTRUMENTS WITH JAW AND FIRING

ACTUATOR LOCKOUT ARRANGEMENTS LOCATED PROXIMAL TO A JAW PIVOT LOCATION;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;

U.S. patent application Ser. No. 18/379,817, titled DUAL INDEPENDENT KEYED LOCKING MEMBERS ACTING ON THE SAME DRIVE MEMBER;

U.S. patent application Ser. No. 18/379,820, titled ADJUNCTS FOR USE WITH SURGICAL STAPLING INSTRUMENTS;

U.S. patent application Ser. No. 18/379,822, titled ADJUNCTS FOR USE WITH SURGICAL STAPLING INSTRUMENTS;

U.S. patent application Ser. No. 18/379,826, titled JAW CONTROL SURFACES ON A SURGICAL INSTRUMENT JAW;

U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE;

U.S. patent application Ser. No. 18/379,831, titled STAPLE CARTRIDGES COMPRISING TRACE RETENTION FEATURES; and U.S. patent application Ser. No. 18/379,832, titled STAPLE CARTRIDGES COMPRISING STAPLE RETENTION FEATURES;

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the described and illustrated embodiments are non-limiting examples, and thus it can be appreciated that the specific structural and functional details disclosed herein may be representative and illustrative. Variations and changes may be made without departing from the scope of the claims.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working frame through which the end effector and elongate shaft of a surgical instrument can be advanced.

FIG. 1 illustrates a block diagram of a surgical system 9002 for use with one or more surgical instruments, tools, and/or robotic systems in accordance with the present disclosure. The system 9002 includes a control circuit 9004. The control circuit 9004 includes a microcontroller 9005 comprising a processor 9006 and a storage medium such as, for example, a memory 9007.

A motor assembly 9009 includes one or more motors, driven by motor drivers. The motor assembly 9009 operably couples to a drive assembly 9011 to drive, or effect, one or more motions at an end effector 9010. The drive assembly 9011 may include any number of components suitable for transmitting motion to the end effector 9010 such as, for example, one or more gears, gear sets, gear transmissions with one or multiple selectable gears, linkages, bars, tubes, and/or cables, for example.

One or more of sensors 9008, for example, provide real-time feedback to the processor 9006 about one or more operational parameters monitored during a surgical procedure being performed by the surgical system 9002. The operational parameters can be associated with a user performing the surgical procedure, a tissue being treated, and/or one or more components of the surgical system 9002, for example. The sensors 9008 may comprise any suitable sensor, such as, for example, a magnetic sensor, such as a Hall effect sensor, a strain gauge, an encoder, a position sensor, a force sensor, a pressure sensor, an inductive sensor, such as an eddy current sensor, a resistive sensor, a capacitive sensor, an optical sensor, and/or any other suitable sensor.

Further to the above, in accordance with the present disclosure, the sensors 9008 may comprise any suitable sensor for detecting one or more conditions at the end effector 9010 including, without limitation, a tissue thickness sensor such as a Hall Effect Sensor or a reed switch sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. As another example, and without limitation, the sensors 9008 may include one or more sensors located at, or about, an articulation joint extending proximally from the end effector 9010. Such sensors may include, for example, a potentiometer, a capacitive sensor (slide potentiometer), piezo-resistive film sensor, a pressure sensor, a pressure sensor, or any other suitable sensor type. In some arrangements, the sensor 9008 may comprise a plurality of sensors located in multiple locations in the end effector 9010, including the staple cartridge, for example.

In accordance with the present disclosure, the surgical system 9002 can include a feedback system 9013 which includes one or more devices for providing a sensory feedback to a user. Such devices may comprise, for example, visual feedback devices (e.g., an LCD display screen, a touch screen, LED indicators), audio feedback devices (e.g., a speaker, a buzzer) or tactile feedback devices (e.g., haptic actuators).

The microcontroller 9005 may be programmed to perform various functions such as precise control over the speed and position of the drive assembly 9011. The microcontroller 9005 may be any single-core or multicore processor such as those known under the trade name ARM Cortex by Texas Instruments. Additionally, the main microcontroller 9005 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 9005 may be configured to compute a response in the software of the microcontroller 9005. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The motor assembly 9009 includes one or more electric motors and one or more motor drivers. The electric motors can be in the form of a brushed direct current (DC) motor with a gearbox and mechanical links to the drive assembly 9011. In accordance with the present disclosure, a motor driver may be an A3941 available from Allegro Microsystems, Inc.

In accordance with the present disclosure, the motor assembly 9009 may include a brushed DC driving motor having a maximum rotational speed of approximately 25,000 RPM. Alternatively, the motor assembly 9009 may include a brushless motor, a synchronous motor, a stepper motor, or any other suitable electric motor. The motor driver may comprise an H-bridge driver comprising field-effect transistors (FETs), for example.

The motor assembly 9009 can be powered by a power source 9012. The power source 9012 can include one or more batteries which may include a number of battery cells connected in series that can be used as the power source to power the motor assembly 9009. In accordance with the present disclosure, the battery cells of the power assembly may be replaceable and/or rechargeable. Further, accordance with the present disclosure, the battery cells comprise lithium-ion batteries which can be couplable to and separable from the power assembly.

Further to the above, the end effector 9010 includes a first jaw 9001 and a second jaw 9003. At least one of the first jaw 9001 and the second jaw 9003 is rotatable relative to the other during a closure motion that transitions the end effector 9010 from an open configuration toward a closed configuration. In accordance with the present disclosure, a cartridge jaw may be movable relative to a fixed anvil jaw to a clamped position. Additionally, an anvil jaw may be movable relative to a fixed cartridge jaw to a clamped position. Furthermore, an anvil jaw and a cartridge jaw may both be movable relative to each other to a clamped position. The closure motion may cause the jaws 9001, 9003 to grasp tissue therebetween. In accordance with the present disclosure, sensors, such as, for example, a strain gauge or a micro-strain gauge, can be configured to measure one or more parameters of the end effector 9010, such as, for example, the amplitude of the strain exerted on the one or both of the jaws 9001, 9003 during a closure motion, which can be indicative of the closure forces applied to the jaws 9001, 9003. The measured strain is converted to a digital signal and provided to the processor 9006, for example. Alternatively, additionally, sensors such as, for example, a load sensor, can measure a closure force and/or a firing force applied to the jaws 9001, 9003.

In accordance with the present disclosure, a current sensor can be employed to measure the current drawn by a motor of the motor assembly 9009. The force required to advance the drive assembly 9011 can correspond to the current drawn by the motor, for example. The measured force is converted to a digital signal and provided to the processor 9006.

In accordance with the present disclosure, strain gauge sensors can be used to measure the force applied to the tissue by the end effector 9010, for example. A strain gauge can be coupled to the end effector 9010 to measure the force on the tissue being treated by the end effector 9010. In accordance with the present disclosure, the strain gauge sensors can measure the amplitude or magnitude of the strain exerted on a jaw of an end effector 9010 during a closure motion which can be indicative of the tissue compression. The measured strain is converted to a digital signal and provided to a processor 9006.

The measurements of the tissue compression, the tissue thickness, and/or the force required to close the end effector on the tissue, as respectively measured by the sensors 9008 can be used by the microcontroller 9005 to characterize the selected position of one or more components of the drive assembly 9011 and/or the corresponding value of the speed of one or more components of the drive assembly 9011. In accordance with the present disclosure, a memory (e.g. memory 9007) may store a technique, an equation, and/or a look-up table which can be employed by the microcontroller 9005 in the assessment.

The system 9002 may comprise wired or wireless communication circuits to communicate with surgical hubs (e.g. surgical hub 9014), communication hubs, and/or robotic surgical hubs, for example. Additional details about suitable interactions between a system 9002 and the surgical hub 9014 are disclosed in U.S. patent application Ser. No. 16/209,423 entitled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981, the entire disclosure of which is incorporated by reference in its entirety herein.

In accordance with the present disclosure, the control circuit 9004 can be configured to implement various processes described herein. The control circuit 9004 may comprise a microcontroller comprising one or more processors (e.g., microprocessor, microcontroller) coupled to at least one memory circuit. The memory circuit stores machine-executable instructions that, when executed by the processor, cause the processor to execute machine instructions to implement various processes described herein. The processor may be any one of a number of single-core or multicore processors known in the art. The memory circuit may comprise volatile and non-volatile storage media. The processor may include an instruction processing unit and an arithmetic unit. The instruction processing unit may be configured to receive instructions from the memory circuit of this disclosure.

Alternatively, the control circuit 9004 can be in the form of a combinational logic circuit configured to implement various processes described herein. The combinational logic circuit may comprise a finite state machine comprising a combinational logic configured to receive data, process the data by the combinational logic, and provide an output.

Alternatively, the control circuit 9004 can be in the form of a sequential logic circuit. The sequential logic circuit can be configured to implement various processes described herein. The sequential logic circuit may comprise a finite state machine. The sequential logic circuit may comprise a combinational logic, at least one memory circuit, and a clock, for example. The at least one memory circuit can store a current state of the finite state machine. In accordance with the present disclosure, the sequential logic circuit may be synchronous or asynchronous. Additionally, the control circuit 9004 may comprise a combination of a processor (e.g., processor 9006) and a finite state machine to implement various processes herein. Furthermore, the finite state machine may comprise a combination of a combinational logic circuit (and the sequential logic circuit, for example.

In accordance with the present disclosure, the staple cartridges described herein are replaceable. The staple cartridge can include one or more electronic systems onboard the staple cartridge. Discussed in greater detail below, one or more of the electronic systems onboard the staple cartridge may be modular and/or replaceable. In accordance with the present disclosure, the electronic systems may be in electrical communication with one or more components of the surgical system 9002. The one or more electronic systems can include, sensor circuits including sensors to measure end effector parameters during a surgical stapling procedure, cartridge-identifying circuits including a circuit with a detectable property to be able to identify one or more properties of the replaceable staple cartridge, and an onboard memory and processor. Additionally, the electronic systems can include a modular electronics package including a PCB, for example, which is attachable to, and detachable from, the replaceable staple cartridge. Furthermore, one or more of the electronic systems may be replaceable with the same or different electronic systems. Such an arrangement can enable a manufacturer or user, for example, to specifically select the desired onboard electronics of the replaceable staple cartridge. For example, different electronics packages may be desired for different types of target tissue. In accordance with the present disclosure, the hardwired electrical pathways between the sensor circuits of the replaceable staple cartridge and the modular electronics package can be modified from electronics package to electronics package.

One or more of the electronic systems of the staple cartridge may also include the method for communicating power and/or data to and/or from the staple cartridge to a control circuit of the overall surgical stapling system (surgical robot, instrument handle, motor control circuits, etc.). In accordance with the present disclosure, power and/or data may be transmitted to and/or from the staple cartridge by way of hardwired connections where physical contact between contacts or connectors of the staple cartridge and contacts or connectors of the cartridge jaw within which the staple cartridge is to be installed is required. In addition to, or in lieu of, the hardwired connections, the staple cartridge and cartridge jaw may each comprise one or more wireless transmission coils to transmit data and/or power to and/or from the staple cartridge.

Figure 2:
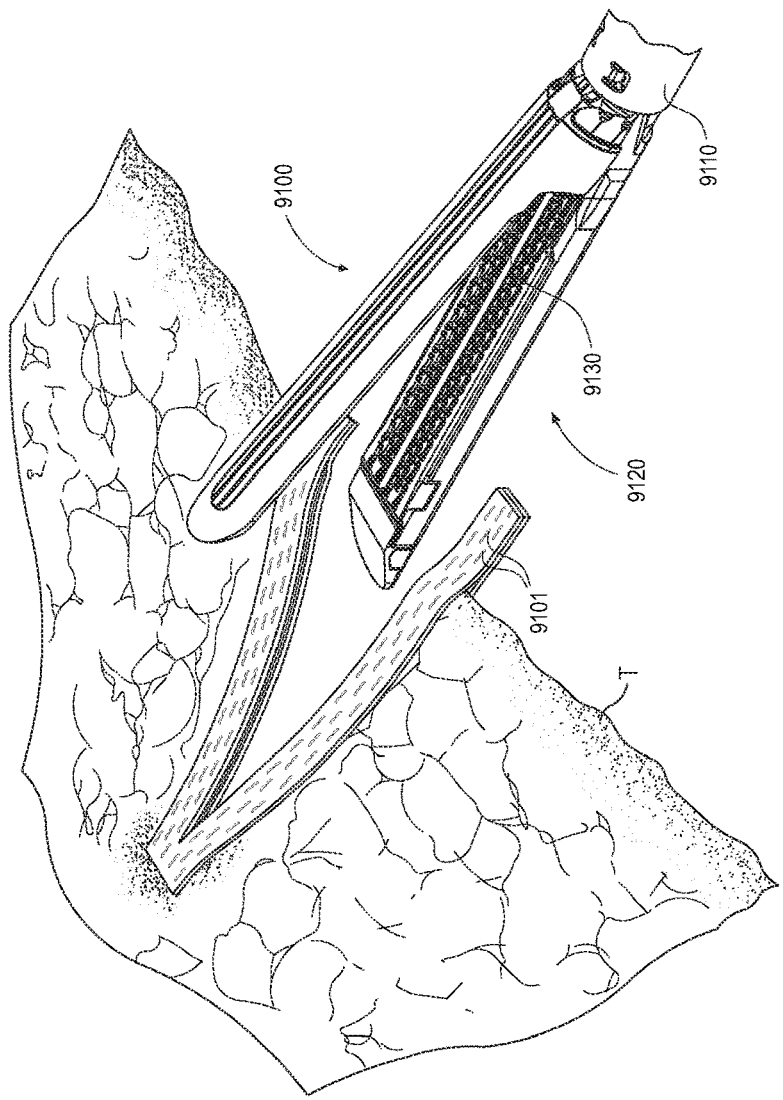
FIG. 2 is a partial perspective view of a surgical stapling assembly and tissue stapled and cut by the surgical stapling assembly, in accordance with the present disclosure.
Figure 4:
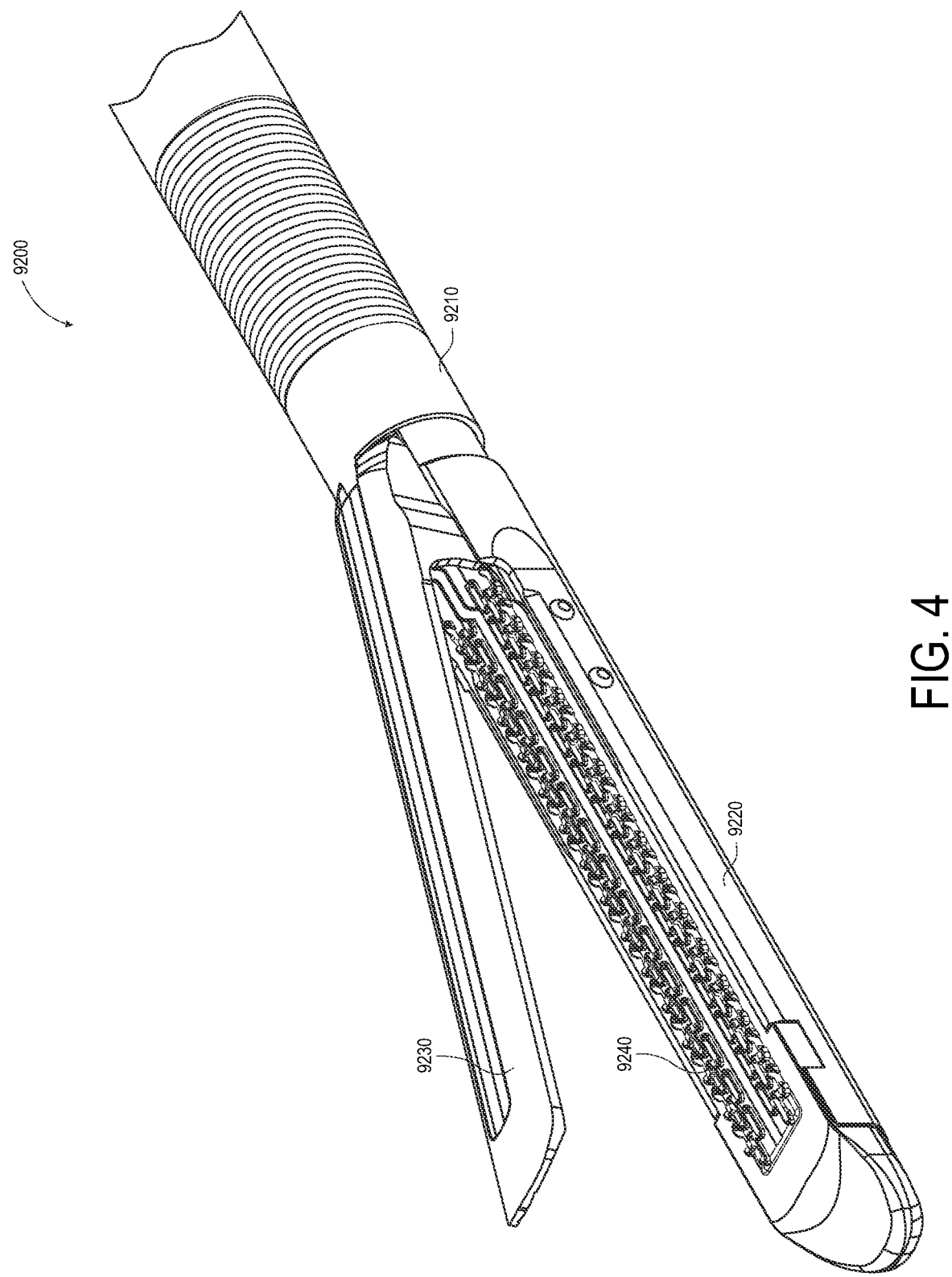
FIG. 4 is a perspective view of a surgical stapling end effector comprising a shaft, a first jaw, a second jaw movable relative to the first jaw, and a replaceable staple cartridge, in accordance with the present disclosure.
Figure 5:
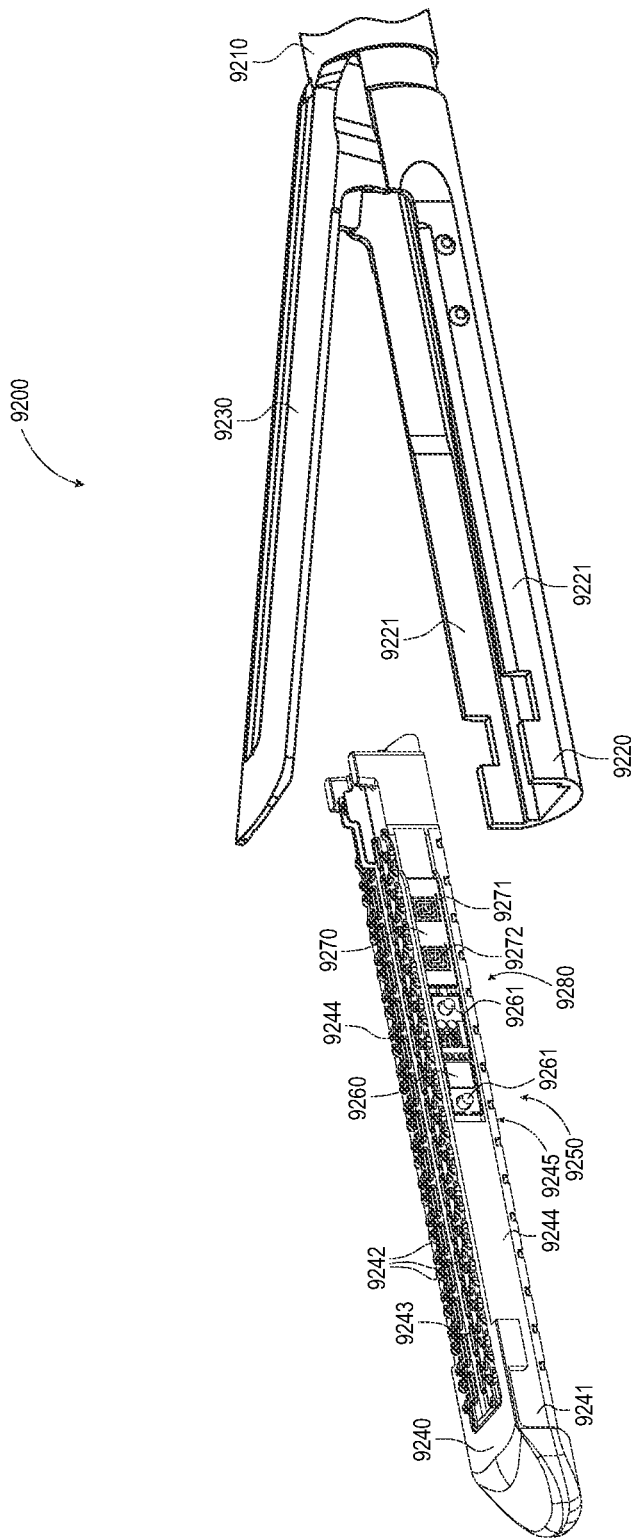
FIG. 5 is a perspective view of the surgical stapling end effector of FIG. 4, wherein the replaceable staple cartridge is illustrated in an uninstalled position, and wherein the replaceable staple cartridge comprises a plurality of onboard electronic systems, and wherein the plurality of onboard electronic systems comprises a modular electronics package and wireless transmission coils.

FIGS. 2 and 3 depict a surgical stapling assembly 9100 configured to clamp, staple, and cut patient tissue T during a surgical stapling procedure. As discussed herein, one or more functions of the surgical stapling assembly 9100 can be motor-driven. The surgical stapling assembly 9100 comprises a shaft 9110 and an end effector 9120 extending from the shaft 9110. The end effector 9120 comprises a cartridge channel jaw 9121 and an anvil jaw 9140 movable relative to the cartridge channel jaw 9121 to clamp tissue therebetween during a clamping stroke. In accordance with the present disclosure, the cartridge channel jaw 9121 can be movable in addition to, or in lieu of, the anvil jaw 9140. The end effector 9120 further comprises a replaceable staple cartridge 9130 configured to be installed into the cartridge channel jaw 9121. The replaceable staple cartridge 9130 comprises a plurality of staples 9101 removably stored therein and configured to be ejected from the replaceable staple cartridge 9130 during a staple firing stroke. In accordance with the present disclosure, the staple cartridge 9130 may not be replaceable. Further, in accordance with the present disclosure, a disposable loading unit may comprise a shaft and an end effector attachable to a control interface. Additionally, the entire cartridge channel jaw 9121 may be replaceable.

The surgical stapling assembly 9100 further comprises a firing driver 9150 actuatable through the end effector 9120 by a drive assembly such as the drive assembly 9011, for example. The firing driver 9150 can comprise any suitable firing driver such as, for example, a distal I-beam head, discussed in greater detail below. The firing driver 9150 is configured to push a sled of the replaceable staple cartridge 9130 from an unfired position to a fired position. During distal translation of the sled within the replaceable staple cartridge 9130, the sled is configured to sequentially lift a plurality of staple drivers with staples 9101 supported thereon. As the drivers are lifted toward the anvil jaw 9140, the drivers are configured to eject the staples 9101 from a plurality of staple cavities and against the anvil jaw 9140.

In accordance with the present disclosure, the sled may be part of the firing driver. Any suitable combination of firing components can be considered the firing driver.

In accordance with the present disclosure, moving the anvil jaw 9140 into a clamped position to clamp tissue between the anvil jaw 9140 and the replaceable staple cartridge 9130 can be performed by a closure driver. The closure driver may be separate from the firing driver 9150 and may be actuatable independently of the firing driver. Alternatively, the closure driver may not be separate from the firing driver 9150. In accordance with the present disclosure, the clamping, or closing, motion may be performed by the firing driver 9150. Opposing jaw-camming pins of a distal I-beam head of the firing driver 9150 are configured to cam the anvil jaw 9140 into a clamped position as the firing driver 9150 is actuated distally through an initial clamping stroke, or motion. In addition to moving the anvil jaw 9140 from an unclamped position to a clamped position during a clamping stroke, the opposing jaw-camming pins are configured to control a tissue gap distance between the anvil jaw 9140 and the replaceable staple cartridge 9130 during the staple firing stroke by limiting the separation of the cartridge channel jaw 9121 and the anvil jaw 9140 during the staple firing stroke with the opposing jaw-camming pins. One of the jaw-camming pins is configured to engage the cartridge channel jaw 9121 and one of the jaw-camming pins is configured to engage the anvil jaw 9140.

In accordance with the present disclosure, the replaceable staple cartridge 9130 may comprise onboard electronics. The onboard electronics require power and/or data transmission to and/or from the replaceable staple cartridge. Thus, an electrical interface exists between the replaceable staple cartridge and the cartridge channel jaw 9121. In accordance with the present disclosure, a control circuit (e.g., control circuit 9004) can be electrically coupleable to the onboard electronics of the replaceable staple cartridge 9130. Any suitable transmission technique can be employed. Various examples are described in greater detail below.

FIGS. 4-8 depict a surgical stapling end effector 9200 comprising a shaft 9210, a cartridge channel 9220, and an anvil 9230 movable relative to the cartridge channel 9220 to clamp tissue therebetween. The surgical stapling end effector 9200 further comprises a replaceable staple cartridge 9240 positioned within the cartridge channel 9220 and containing staples deployable by a firing driver during a firing stroke. The replaceable staple cartridge 9240 comprises a cartridge body 9241 comprising a plurality of staple cavities 9242, a longitudinal slot 9243, and sidewalls 9244. One of the sidewalls 9244 comprises a receptacle 9245. The replaceable staple cartridge 9240 comprises onboard electronics 9250 comprising a modular electronics package 9260 and a wireless transmission interface 9270 configured to transmit one of power and/or data to and/or from the replaceable staple cartridge 9240 to and/or from the control circuit 9004 of the surgical system 9002 with which the surgical stapling end effector 9200 is used.

The onboard electronics, or electronics sub-assembly, 9250 are positioned within the receptacle 9245. The receptacle 9245 can be configured to receive one or more modular electronics packages 9260. In accordance with the present disclosure, when installed in the receptacle 9245, the modular electronics packages 9260 can be electrically coupled with the wireless transmission interface 9270 via electrical traces 9280 positioned within the receptacle 9245. Additionally, in accordance with the present disclosure, additional electrical traces can be employed to connect the receptacle 9245 (and, thus, the electronics package 9260 and/or wireless transmission interface 9270) to various sensors onboard the staple cartridge 9240. The modular electronics package 9260 comprises a PCB including a processer and a memory. However, any suitable modular electronics package 9260 can be employed with any suitable electrical components such as sensors, multiple processors, multiple memories, etc. The modular electronics package 9260 is pinned to the sidewall 9244 via attachment pins 9261. A user may replace the modular electronics package 9260 with a different modular electronics package 9260 by disengaging the pins 9261, removing the modular electronics package 9260, placing a different modular electronics package in place of the modular electronics package 9260, and re-engaging the pins 9261. Each modular electronics package 9260 may comprise attachment pins which can be press fit, or snap fit, into corresponding apertures defined in the receptacle 9245 such that the pins remain a part of the modular electronics package 9260.

In accordance with the present disclosure, the one or more modular electronics packages 9260 can be electrically coupled with onboard electrical circuits of the replaceable staple cartridge 9240 such as, for example, sensor circuits including sensors for measuring one or more end effector parameters, lockout circuits for identifying of the staple cartridge is spent or unspent, cartridge-identifying circuits for identifying the specific type, size, length, and/or color, of the staple cartridge 9240, and/or RFID circuits, etc. The signals received from the various onboard circuits can be communicated to the modular electronics package 9260. In accordance with the present disclosure, the signals received from the various onboard circuits can be communicated to the control circuit 9004 of the surgical system 9002 with which the staple cartridge 9260 is used in addition to, or in lieu of, to the modular electronics package 9260. The onboard circuits can be powered through the onboard electronics package 9260. Additionally, the onboard circuits can receive power directly from the wireless transmission interface 9270. Multiple power sources may be employed. Further, accordance with the present disclosure, one or more of the power sources used can act as backup power sources.

As discussed above, the wireless transmission interface 9270 is configured to transmit data and/or power to the control circuit 9004 of the surgical system 9002. The wireless transmission interface 9270 comprises a proximal transmission coil 9271 and a distal transmission coil 9272. In accordance with the present disclosure, one of the coils may transmit data therethrough and the other coil may transmit power therethrough. The wireless transmission interface 9270 is configured to transmit the power and/or data to and/or from the modular electronics package 9260 through electrical traces 9280. In accordance with the present disclosure, the modular electronics package 9260 may comprise contacts configured to engage the electrical traces 9280 upon installation of the modular electronics pack 9260 into the receptacle 9245.

Figure 6:
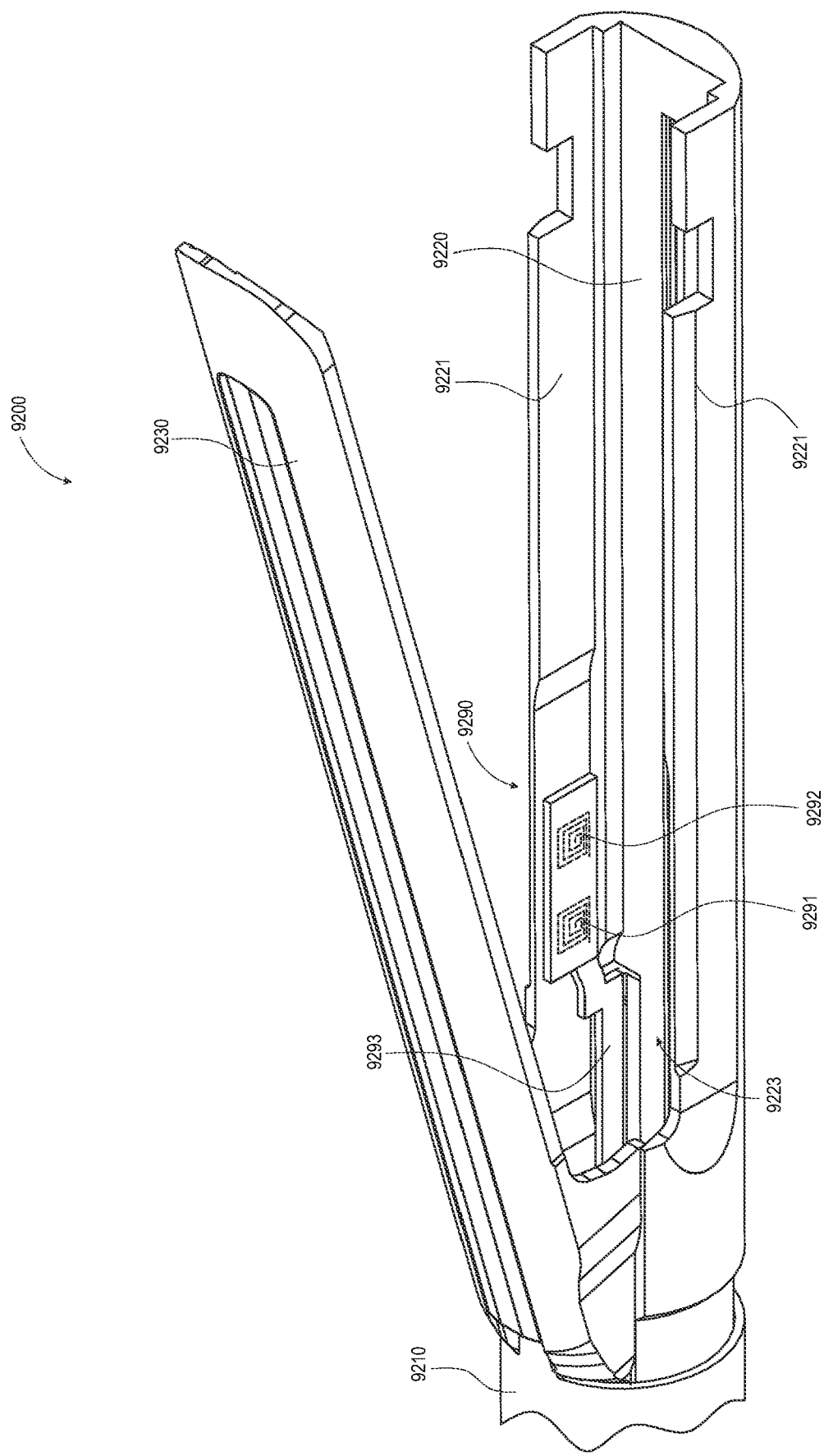
FIG. 6 is a perspective view of the first jaw and the second jaw of FIG. 4, wherein the first jaw comprises a cartridge channel comprising corresponding wireless transmission coils configured to transmit power and/or data to and/or from the replaceable staple cartridge upon installation of the replaceable staple cartridge into the cartridge channel.

Referring to FIG. 6, the cartridge channel jaw 9220 comprises channel sidewalls 9221. The surgical stapling end effector 9200 further comprises a wireless transmission interface 9290 attached to one of the channel sidewalls 9221. The wireless transmission interface 9290 comprises a proximal transmission coil 9291 and a distal transmission coil 9292. The wireless transmission interface 9290 further comprises a flex circuit 9292 at least partially positioned within a slot 9223 defined in the cartridge channel jaw 9220. Once the replaceable staple cartridge 9260 is properly installed in the cartridge channel jaw 9220, the proximal wireless transmission coils 9271, 9291 are sufficiently aligned to wireless transmit power and/or data therethrough and the distal wireless transmission coils 9272, 9292 are sufficiently aligned to wireless transmit power and/or data therethrough. In accordance with the present disclosure, the control circuit 9004 can be configured to alert a user upon obtaining proper alignment between the coils 9271, 9272, 9291, 9292. Additionally, one pair of the coils may transmit power and one pair of the coils may transmit data. The wireless transmission interfaces 9270, 9290 can comprise any suitable material to host the wireless transmission coils and connect the coils to the outgoing/ingoing electrical pathways (such as the flex circuit 9293 and electrical traces 9280, for example).

Figure 7:
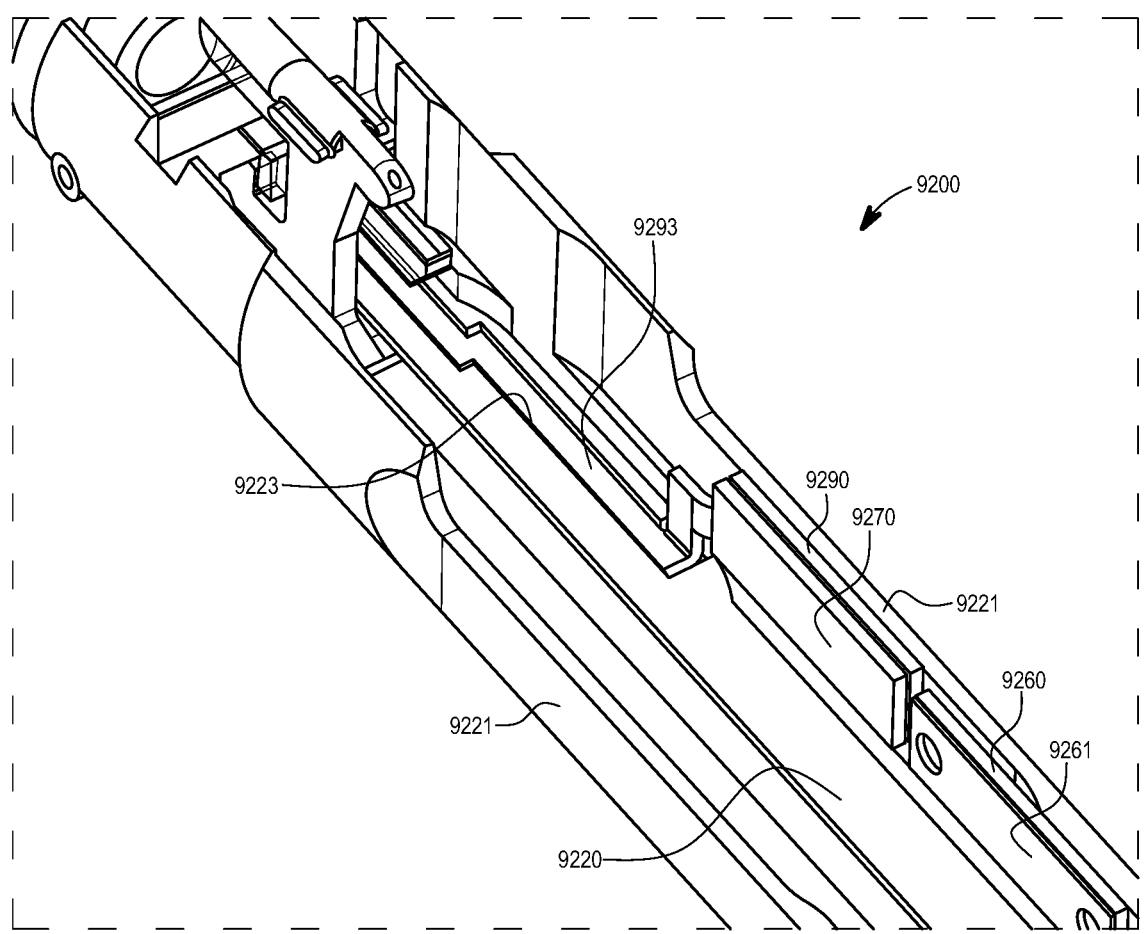
FIG. 7 is a perspective view of the first jaw of FIG. 4 illustrating the wireless transmission coils of the first jaw and the replaceable staple cartridge and the modular electronics package.
Figure 8:
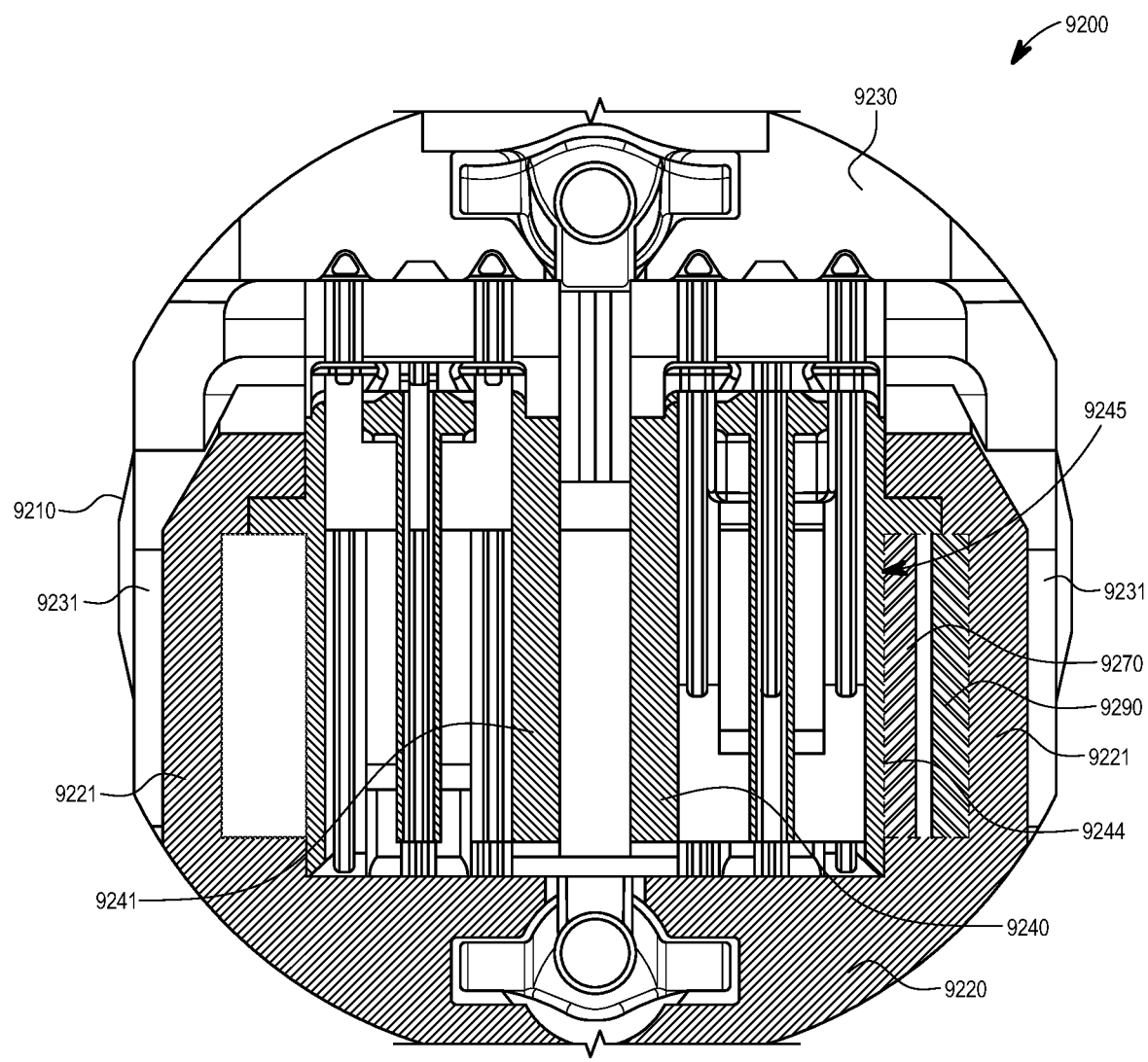
FIG. 8 is a cross-sectional view of the surgical stapling end effector of FIG. 4.

As can be seen in FIG. 7, the flex circuit 9293 is positioned within the slot 9223 of the cartridge channel jaw 9220. The flex circuit 9293 electrically couples the wireless transmission interface 9290 (specifically the coils 9291, 9292) to the control circuit 9004 of the surgical system 9002 to supply the coils 9291, 9292 with data and/or power. The flex circuit 9293 is configured to run proximally toward a surgical instrument control interface such as, for example, a surgical instrument handle and/or robot puck interface, for example.

Described herein are a plurality of onboard electronics of a replaceable surgical staple cartridge. In accordance with the present disclosure, one or more of the onboard electronics can be identifiable, or detectable, by the control circuit 9004 of the surgical system 9002. Certain control algorithms can be selected and/or adjusted based on the specific onboard electronics. For example, a clinician may plan a procedure targeting a specific type of tissue. The specific type of tissue may require a specific length, type, or color staple cartridge. The specific type of tissue may also require a specific firing algorithm. For example, the specific type of tissue may be thinner than other types of tissue and a slower, more delicate, firing and/or clamping control algorithm may be selected by the control circuit 9004.

When the control circuit 9004 selects a specific control algorithm, the onboard electronics can be utilized in a specific predetermined manner. For example, a sensor circuit onboard a replaceable staple cartridge can be utilized to detect a tissue density, for example, regardless of which modular electronics package is installed in the staple cartridge. The measured tissue density can be used during firing to modify the firing control algorithm. However, depending on which modular electronics package (selected for a specific type of tissue) is installed, the firing control algorithm can be modified differently for the same tissue density measurement with a different modular electronics package (associated with a different type of tissue) installed in the stapling end effector. Such an arrangement can allow a user to change the onboard control circuit by swapping the modular electronics package with a different modular electronics package to accommodate the specific procedure within which the staple cartridge is to be used. The selected control circuit may process sensor circuit values differently depending on the type of tissue associated with that modular electronics package.

Changing the modular electronics package may also be performed to update the software, firmware, and/or other control programs/algorithms of the replaceable staple cartridge. In accordance with the present disclosure, the replaceable staple cartridge can be manufactured and the modular electronics package can be updated over time so the physical design of the replaceable staple cartridge need not change overtime as the control algorithms/programs are updated. Upon distributing the replaceable staple cartridge, the most up to date modular electronics package can be easily and quickly installed on the replaceable staple cartridge. New modular electronics packages can be designed to fit in the existing cartridge receptacle.

Figure 9:
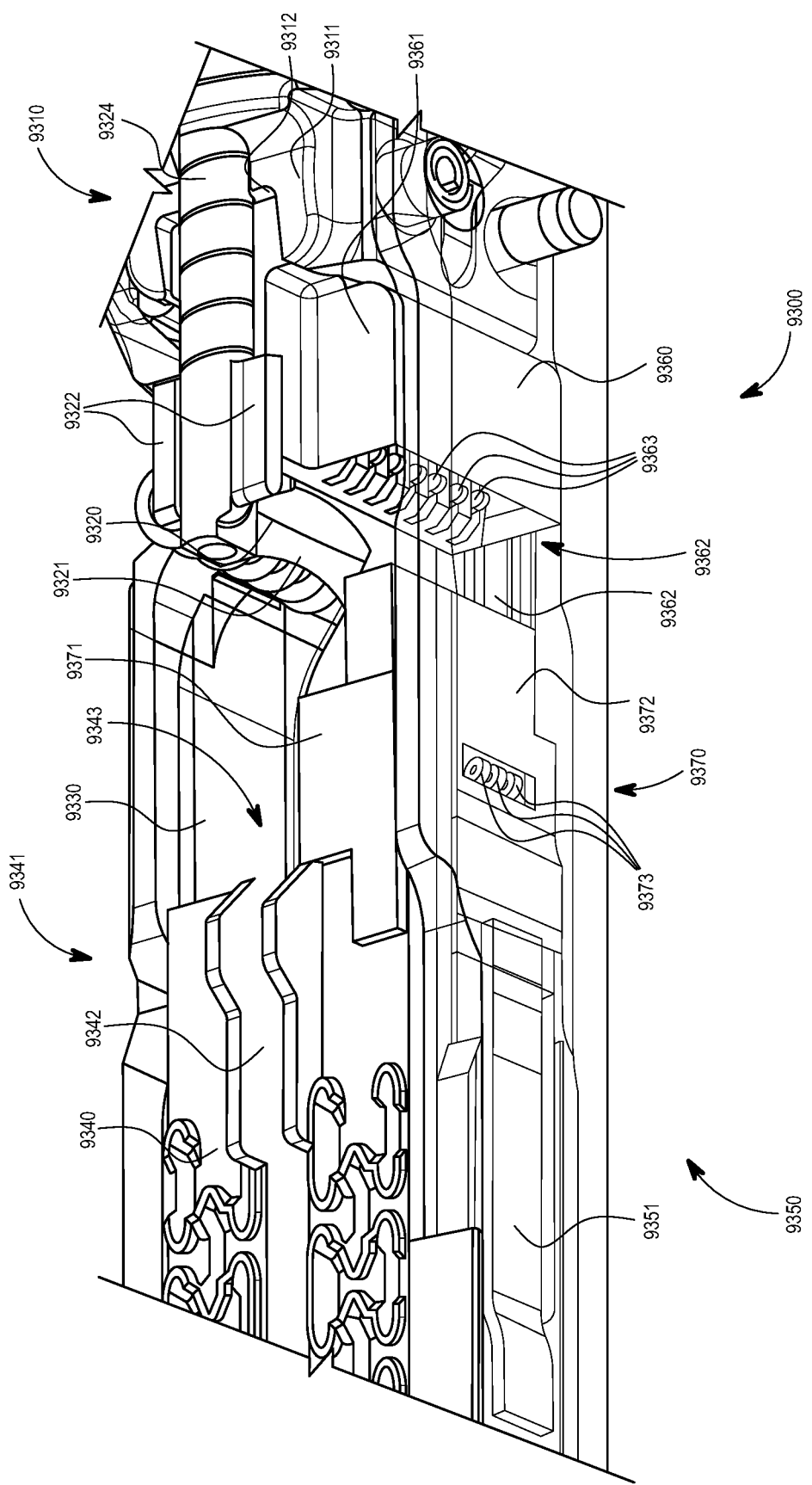
FIG. 9 is a perspective view of a portion of a surgical stapling end effector comprising a first jaw, a second jaw, and a replaceable staple cartridge positionable within the first jaw (illustrated in a partially installed position), wherein the replaceable staple cartridge comprises an electrical connector at the proximal end couplable with a corresponding electrical connector positioned within the first jaw in accordance with the present disclosure.
Figure 10:
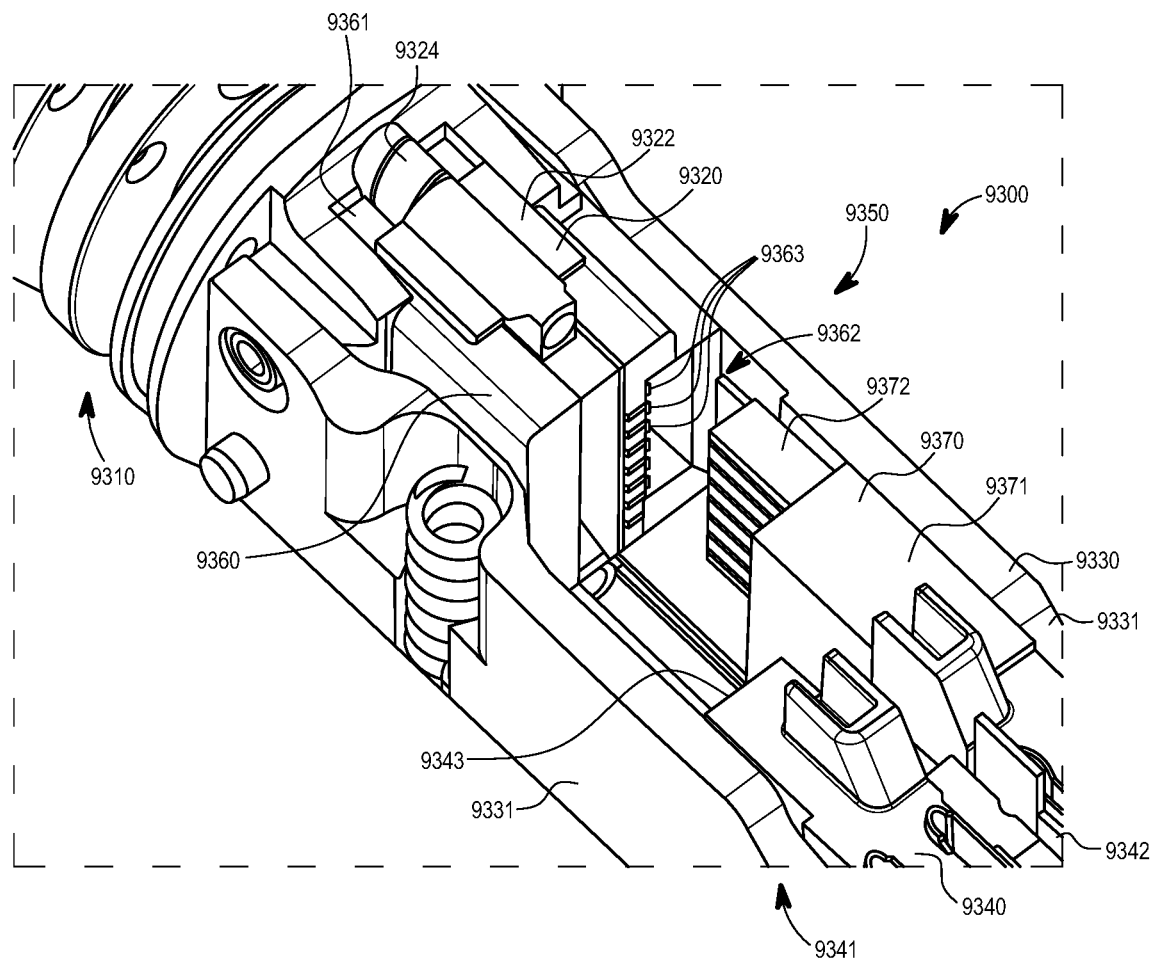
FIG. 10 is a perspective view of the surgical stapling end effector of FIG. 9.

FIGS. 9 and 10 depict a surgical stapling end effector 9300 comprising a shaft assembly 9310 including a channel retainer 9311, a cartridge channel jaw 9330 supported by the channel retainer 9311, and a replaceable staple cartridge 9340 configured to be installed into the cartridge channel jaw 9330. The surgical stapling end effector 9300 further comprises a firing driver 9320 including a cutting edge to cut tissue, anvil cams 9322 to engage the anvil during a firing stroke, and channel cams 9323 to engage the cartridge channel jaw 9330 during the firing stroke. The firing driver 9320 is illustrated in its proximal-most position or, an unfired position.

The replaceable staple cartridge 9340 comprises a proximal end 9341, a slot 9342 configured to receive at least a portion of the firing drive 9320 during the firing stroke, and a proximally-facing side 9343. The replaceable staple cartridge 9340 further comprises an electronic system 9350. The electronic system 9350 may comprise any suitable electronic components such as those disclosed herein. For example, the replaceable staple cartridge 9340 comprises a wireless transmission interface, one or more onboard sensor circuits, one or more onboard cartridge identifier circuits, and/or one or more modular electronics packages. One or more of the electronic components are configured to receive power and/or data from the surgical instrument (surgical robot and/or surgical instrument handle, for example) to which the replaceable staple cartridge 9340 is attached. The electronic system 9350 of the replaceable staple cartridge 9340 further comprises electrical connectors 9360, 9370 through which power and/or data is transferred.

The electrical connector 9360 is positioned within the cartridge channel jaw 9330 and at least a portion of the channel retainer 9311. The electrical connector 9360 comprises a female slot 9362 configured to receive a male end 9372 of the electrical connector 9370. The electrical connector 9360 comprises a body 9361 at least partially positioned within a slot 9312 of the channel retainer 9311. As can be seen in FIGS. 9 and 10, the electrical connector is positioned proximal to the cutting edge 9321 when the firing driver 9320 is in its unfired position. The electrical connector 9360 further comprises a plurality of contacts 9363 positioned within the female slot 9361 and configured to be engaged by a plurality of corresponding contacts 9373 of the electrical connector 9370. The male end 9372 extends proximally from a body 9371 of the electrical connector 9370. As can be seen in FIG. 9, the electrical connector 9370 extends proximally from the proximal-facing side 9343 of the replaceable staple cartridge 9340.

The replaceable staple cartridge 9340 is configured to be slid proximally into the cartridge channel jaw 9330. This distal-to-proximal installation motion allows the male end 9372 of the electrical connector 9370 to be inserted into the female slot 9362 of the electrical connector 9360 when installing the replaceable staple cartridge 9340 into the cartridge channel jaw 9330. Once connected, power and/or data may be transferred through the contacts 9363, 9373. The electronic system 9350 further comprises an electrical cable 9351 connected to the contacts 9373 to carry electrical signals to the various onboard electronics of the replaceable staple cartridge 9340. The various onboard electronics of the replaceable staple cartridge 9340 may receive electrical signals from the electrical connector 9370 individually. As can be seen in FIG. 10, the cartridge channel jaw 9330 comprises channel sides 9331 configured to support the replaceable staple cartridge 9340 during and after installation of the replaceable staple cartridge 9340 into the cartridge channel jaw 9330. The electrical cable 9351 is positioned between the cartridge channel jaw 9330 and a sidewall of the replaceable staple cartridge 9340.

Figure 11:
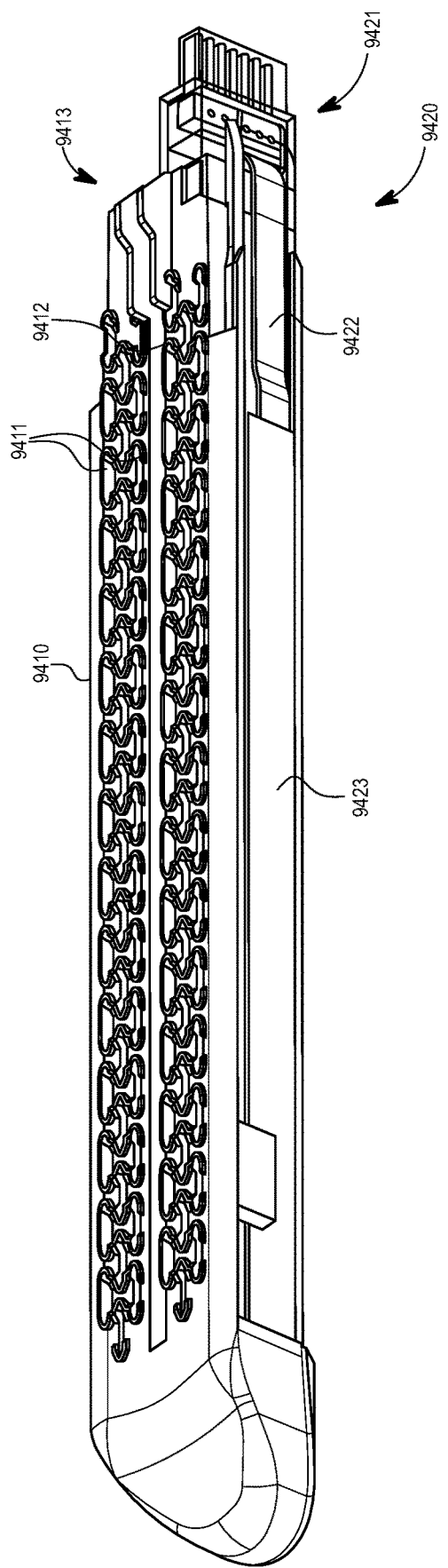
FIG. 11 is a perspective view of a replaceable staple cartridge comprising onboard electronics and an electrical connector extending from a proximal end of the replaceable staple cartridge in accordance with the present disclosure.

FIG. 11 is a perspective view of a replaceable staple cartridge 9400 for use with a surgical system such as those disclosed herein. The replaceable staple cartridge 9400 is configured to be installed into a cartridge channel jaw of a surgical stapling end effector. The replaceable staple cartridge 9400 comprises a cartridge body 9410 comprising a plurality of staple cavities 9411, a longitudinal slot 9412, and a proximal end 9413. The replaceable staple cartridge 9400 comprises an electrical system 9420 comprising an electrical connector 9421 extending from the proximal end 9413 of the cartridge body 9410, an electrical cable 9422 electrically coupled to the electrical connector 9421, and onboard electronics 9423 electrically coupled to the electrical connector 9421.

The onboard electronics 9423 can comprise any suitable onboard electronics such as those disclosed herein. In accordance with the present disclosure, the onboard electronics 9423 may comprise a modular electronics package, a PCB including a processor and a memory among other electrical components, a wireless transmission interface, one or more sensor circuits electrically coupled to the electrical connector 9421 and/or the modular electronics package, PCB, and/or the wireless transmission interface, and/or one or more cartridge-identifier circuits electrically coupled to the electrical connector 9421 and/or the modular electronics package, PCB, and/or the wireless transmission interface.

In accordance with the present disclosure, one or more modular electronics packages may be capable of being installed into a receptacle of a replaceable staple cartridge. Where multiple modular electronics packages (PCBs, for example) are installed into the receptacle, each modular electronics package is electrically coupled to each other. Additionally, each modular electronics package can be electrically coupled to the control circuit 9004 independently through the electrical connector of the replaceable staple cartridge. In accordance with the present disclosure, the entire receptacle may contain multiple sets of electrical contacts for each component installed in the receptacle. Each set of electrical contacts can be electrically coupled to the wireless transmission interface and/or the electrical connector.

In accordance with the present disclosure, all of the electrical components installed in the receptacle of a replaceable staple cartridge can be powered through a wireless coil of the wireless transmission interface (and thus the corresponding wireless transmission interface of the cartridge channel jaw) and receive and/or transmit data through another wireless coil of the wireless transmission interface (and thus the corresponding wireless transmission interface of the cartridge channel jaw). In accordance with the present disclosure, one or more of the electrical components installed in the receptacle may be battery powered.

In addition to, or in lieu of, receiving power and data through a wireless transmission interface, the electrical components installed in the receptacle of a replaceable staple cartridge are electrically coupled to the surgical instrument through the electrical connector of the replaceable staple cartridge to receive power and/or data therethrough. Such an electrical connection can serve as a redundancy, or back up, path of electrical power and/or data to and/or from the replaceable staple cartridge. In accordance with the present disclosure, some of the electrical components of a replaceable staple cartridge can be electrically coupled to the surgical instrument through the electrical connector, while others can be electrically coupled to the surgical instrument through the wireless transmission interface. Additionally, in accordance with the present disclosure, all of the data transfer may be achieved through the hardwired interface and all of the power transfer may be achieved through the wireless transmission interface. Alternatively, all of the power transfer may be achieved through the hardwired interface and all of the data transfer may be achieved through the wireless transmission interface. In accordance with the present disclosure, certain components of the staple cartridge may receive power through the hardwired interface and certain components of the staple cartridge may receive power through the wireless transmission interface. Alternatively, in accordance with the present disclosure, certain components of the staple cartridge may receive data through the hardwired interface and certain components of the staple cartridge may receive data through the wireless transmission interface.

Figure 12:
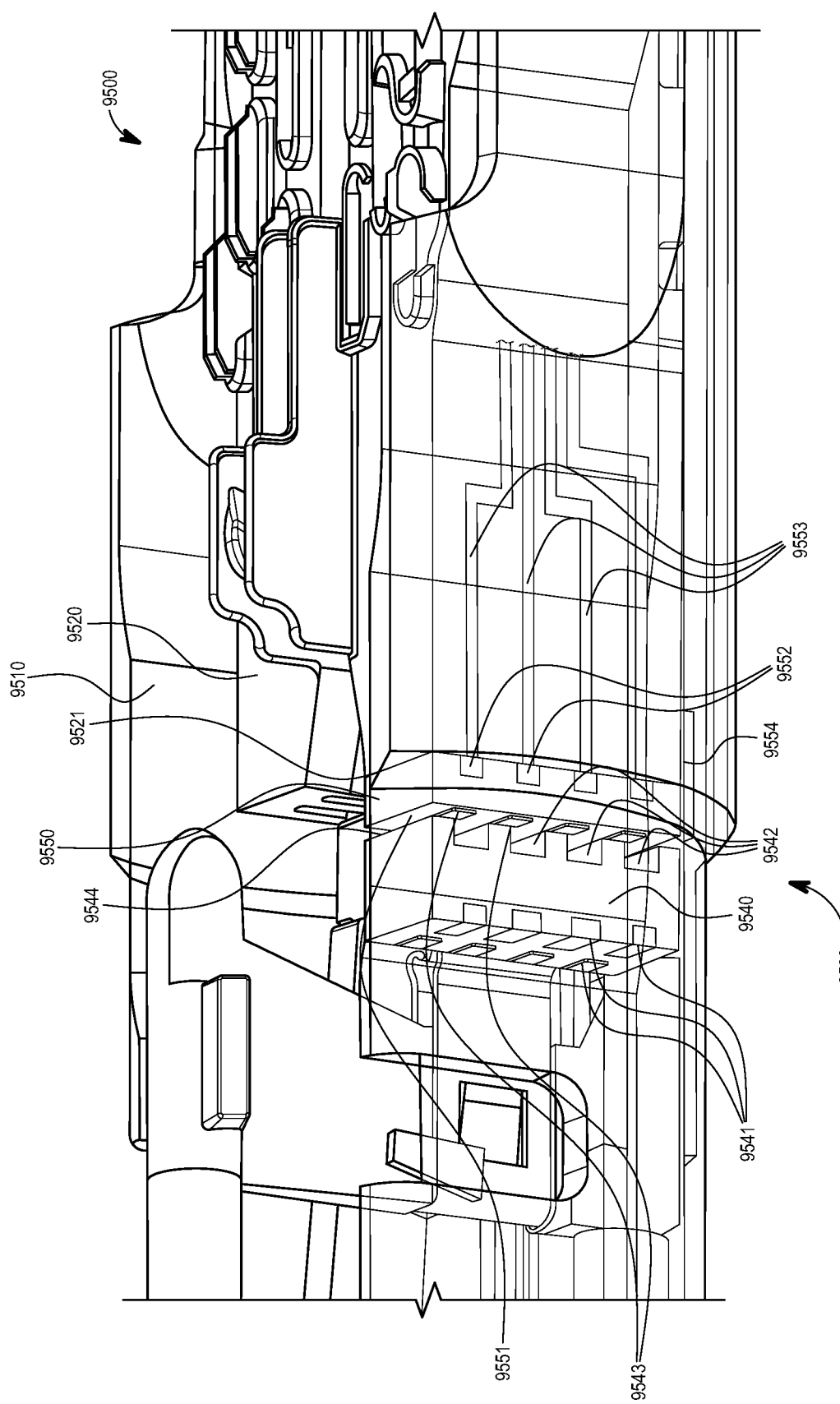
FIG. 12 is a perspective view of a surgical stapling end effector comprising a cartridge channel jaw, a replaceable staple cartridge configured to be installed in the cartridge channel jaw, and an electronic system comprising an electrical connector positioned at a proximal end of the replaceable staple cartridge and a corresponding electrical connector positioned within the first jaw configured to be electrically coupled to the electrical connector of the replaceable staple cartridge in accordance with the present disclosure.
Figure 13:
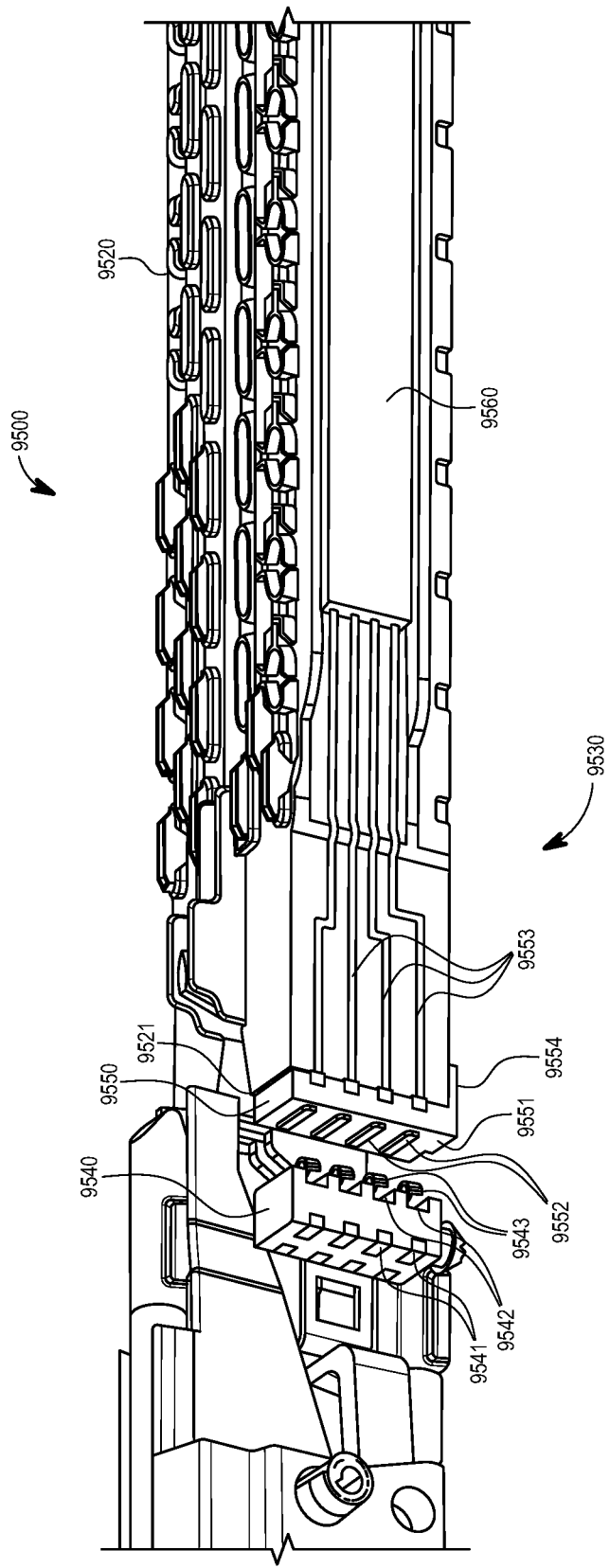
FIG. 13 is a perspective view of a portion of the surgical stapling end effector of FIG. 12.

FIGS. 12 and 13 depict a surgical stapling end effector 9500 including a cartridge channel jaw 9510, a replaceable staple cartridge 9520 having onboard electronics 9560, and an electrical connector system 9530 configured to transmit data and/or power between the onboard electronics 9560 and the control circuit 9004 of the surgical system 9002, for example. The electrical connector system 9530 comprises a proximal connector 9540 positioned within the cartridge channel jaw 9510 and a distal connector 9530 mounted to a proximal face 9521 of the replaceable staple cartridge 9520. The proximal connector 9540 comprises proximal contacts 9541 electrically coupled with a cable, for example, to carry electrical signals to and/or from the control circuit 9004 positioned within a surgical instrument handle, shaft, and/or robotic puck, for example. The proximal connector 9540 comprises a distal end 9544 having a plurality of slots 9542 and electrical connectors 9543 extending out of the slots 9542 and electrically coupled to the proximal contacts 9541.

The distal connector 9550 is mounted to the proximal face 9521 and comprises a tab 9554 extending underneath a bottom of a cartridge body of the replaceable staple cartridge 9520. The tab 9554 may serve to support the replaceable staple cartridge 9520 against the cartridge channel jaw 9510 upon installation. In accordance with the present disclosure, the tab 9554 may serve as an alignment aid for aligning the proximal connector 9540 and the distal connector 9550 during and/or after installation of the replaceable staple cartridge 9520 in the cartridge channel jaw 9530. The distal connecter 9550 comprises electrical contacts 9552 extending from a proximal side 9551 of the connector 9550, through the connector 9550, and electrically coupled to electrical traces, or leads, 9553 distal to the connector 9550. In accordance with the present disclosure, the electrical traces 9553 can be positioned within slots, or channels, defined in the cartridge body of the replaceable staple cartridge 9540. The electrical traces 9553 are configured to carry electrical signals to and/or from onboard electronics 9560.

In accordance with the present disclosure, the electrical connectors 9543 may be spring loaded such that, as the replaceable staple cartridge 9520 is installed in the cartridge channel jaw 9510 in a distal-to-proximal direction, the electrical connectors 9542 are able to be engaged by and pushed into the slots, as necessary, by corresponding contacts 9552 upon installation of the replaceable staple cartridge 9520 into the cartridge channel jaw 9510 to affirmatively bias the connectors 9542 into engagement with the contacts 9552.

In accordance with the present disclosure, the one or more onboard electronics discussed herein may be installed into a cartridge channel jaw in addition to, or in place of, onboard electronics installed on a replaceable staple cartridge.

Figure 14:
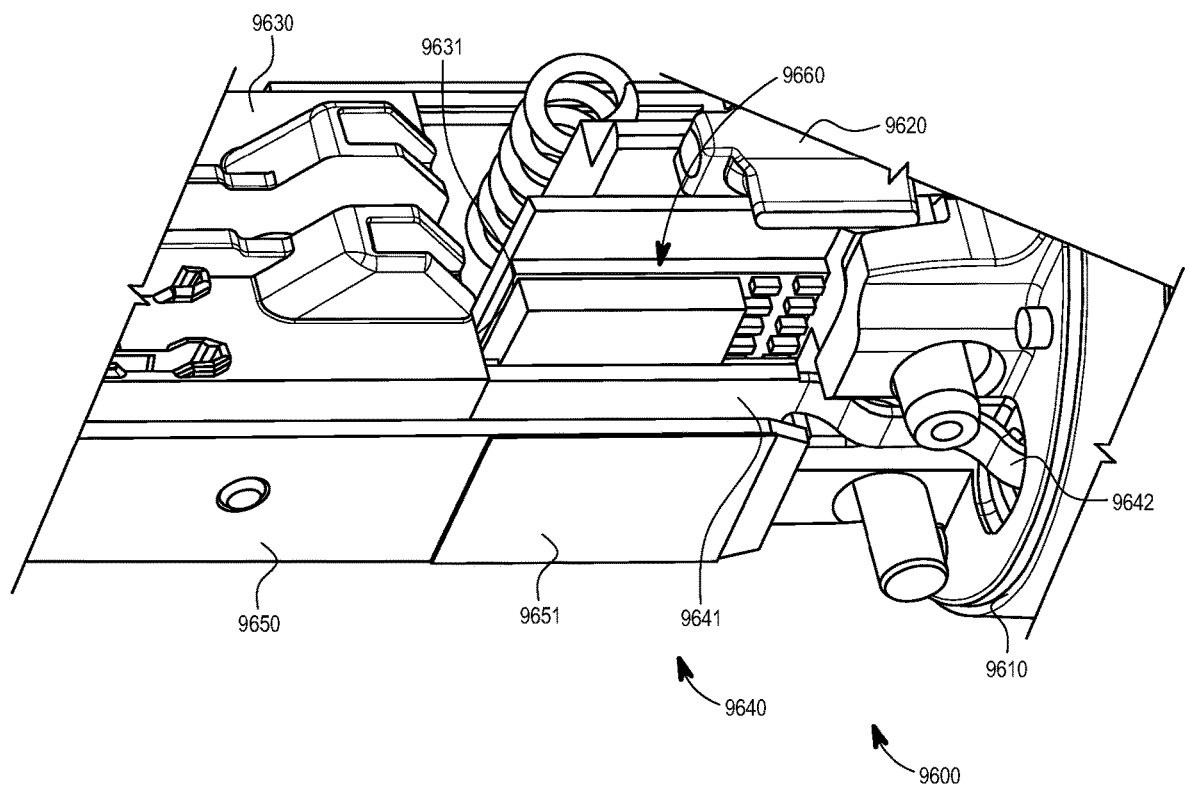
FIG. 14 is a perspective view of a portion of a surgical stapling end effector comprising a replaceable staple cartridge configured to be installed in a jaw of the surgical stapling end effector and an electronics interface comprising wireless transmission coils to communicate power and/or data to and/or from the replaceable staple cartridge in accordance with the present disclosure.

FIG. 14 depicts a surgical stapling assembly 9600 comprising a shaft assembly 9610 and a replaceable staple cartridge 9630. The replaceable staple cartridge 9630 is configured to be installed into a cartridge channel jaw. The surgical stapling assembly 9600 further comprises an electrical system 9640 comprising a PCB 9650 having a wireless transmission interface, or coils, 9651 integrated into the PCB 9650 and a wireless transmission interface, or coil, 9641 configured to transfer power and/or data to and/or from the wireless transmission interface 9651. The wireless transmission interface 9641 is supplied with electrical data and/or power through a cable 9642.

The surgical stapling assembly 9600 further comprises a firing drive 9620 and an electronics assembly 9660 positioned between the replaceable staple cartridge 9630 and the shaft assembly 9610. The electronics assembly 9660 can be configured to receive power and/or data from the wireless transmission interface 9641. In accordance with the present disclosure, the electronics assembly 9660 may comprise onboard sensor circuits configured to measure one or more parameters of the firing driver 9620 during a firing stroke. This information can be transmitted to the PCB 9650 and/or back to a control circuit of the surgical instrument through the cable 9642. As can be seen in FIG. 14, the wireless transmission interface 9651 is proximal to a proximal end 9631 of the replaceable staple cartridge 9630. In accordance with the present disclosure, the PCB 9650 may be attachable to and/or detachable from the replaceable staple cartridge 9630. Additionally, the PCB 9650 may be attachable to and/or detachable from a cartridge channel jaw.

FIGS. 15-19 depict an electrical connector arrangement comprising a male connector 9670 and a female connector 9680 configured to receive the male connector 9670. The connector arrangement can be used with a replaceable staple cartridge and a cartridge channel jaw where one of the connectors 9670, 9680 is attached, or mounted, to the replaceable staple cartridge and the other of the connectors 9670, 9680 is attached, or mounted, to the cartridge channel jaw. In accordance with the present disclosure, the electrical connector connected to the cartridge can be mounted to the bottom of the replaceable staple cartridge near the distal end and the electrical connector can be mounted to the end of the cartridge channel jaw. In such an arrangement, the replaceable staple cartridge can be inserted into the jaws at an angle, brought down at least substantially parallel to the cartridge channel jaw, and pushed fully proximally to seat the cartridge into the jaw which also physically couples the electrical connectors.

The male connector 9670 comprises a connector body 9671 having a male end 9672. Electrical contacts 9673 are exposed on the male end 9672. The male connector 9670 further comprises alignment fins 9674 extending from the connector body 9671 to the male end 9672. In accordance with the present disclosure, the fins 9674 may provide additional support, or rigidity, to the male end 9672. The female connector 9680 comprises a connector body 9681 having a female end 9682. Electrical contacts 9683 are exposed inside of the female end 9682. The female end 9682 further comprises slots 9684 defined in the female end to receive the fins 9674 of the male end 9672 upon complete insertion of the male end 9672 into the female end 9682. As can be seen in FIG. 19, the connectors 9670, 9680 are fully connected where electrical signals from electrical cables 9675, 9685 may be transmitted therebetween by way of the contacts 9673, 9683.

Figure 20:
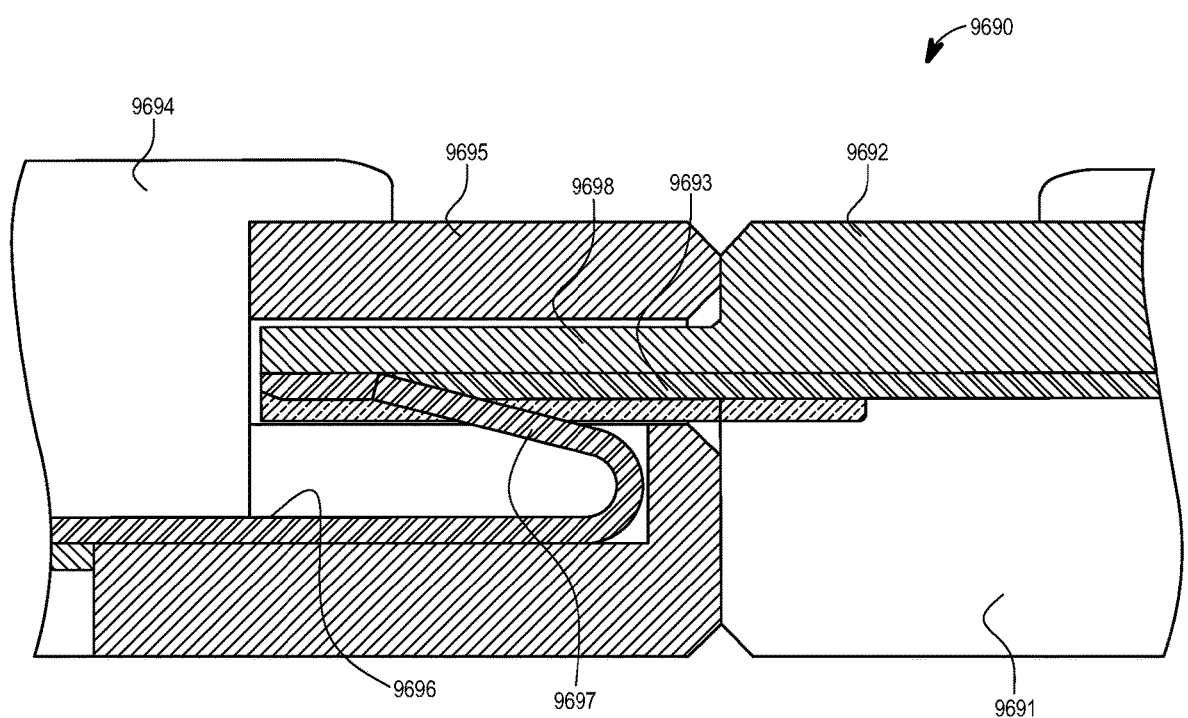
FIG. 20 is an elevational view of an electrical connector system of a surgical stapling end effector in accordance with the present disclosure.

FIG. 20 depicts an electrical connector arrangement 9690 between a cartridge channel jaw 9691 and a replaceable staple cartridge 9694. The cartridge channel jaw 9691 comprises an electrical connector 9692 having a male end 9698 and an electrical contact 9693 exposed on the male end 9698. The replaceable staple cartridge 9694 comprises a female electrical connector 9695 having an electrical contact 9696 exposed inside of the female electrical connector 9695. The electrical contact 9696 has a spring end 9697 configured to engage the electrical contact 9693 of the male end 9698 upon insertion of the male end 9698 into the female electrical connector 9695. In accordance with the present disclosure, the replaceable staple cartridge may comprise the male electrical connector and the cartridge channel jaw may comprise the female electrical connector.

Figure 21:
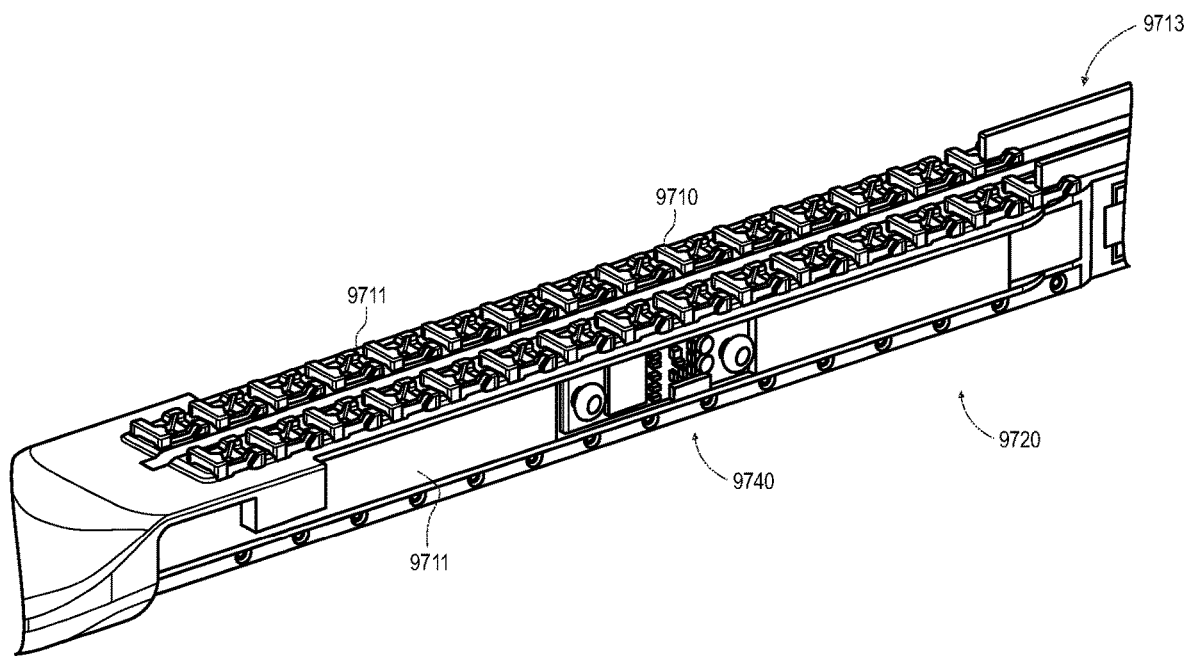
FIG. 21 is a perspective view of a replaceable staple cartridge comprising onboard electronics systems including a modular electronics package, a wireless transmission coil interface, and an electrical circuit indicative of one or more properties of the replaceable staple cartridge detectable by a surgical instrument in accordance with the present disclosure.
Figure 22:
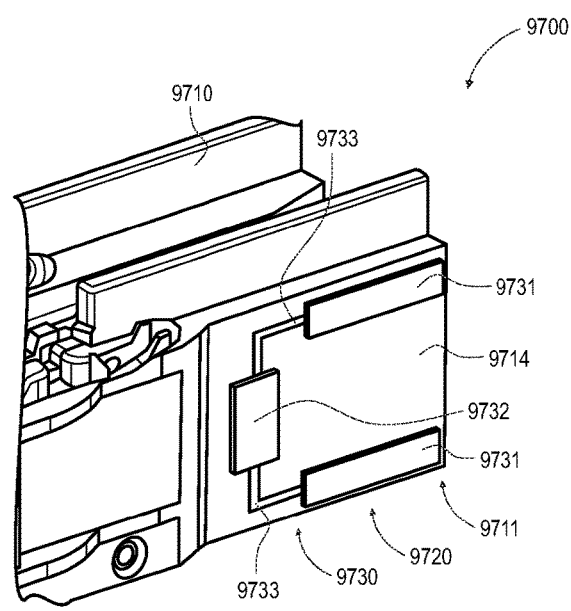
FIG. 22 is a partial perspective view of replaceable staple cartridge of FIG. 21.

FIGS. 21 and 22 depict a replaceable staple cartridge 9700 for use with one or more of the surgical systems disclosed herein. The replaceable staple cartridge 9700 comprises a cartridge body 9710 having cartridge sides 9711 and a proximal end 9713. The replaceable staple cartridge 9700 further comprises onboard electronics 9720. The onboard electronics 9720 comprise any suitable electronic component disclosed herein and combinations thereof. The onboard electronics 9720 comprise a modular electronics package 9740 replaceably attached to a side 9711 of the cartridge body 9710. The onboard electronics 9720 further comprise a cartridge-identifier circuit 9730 on a side 9714 of the proximal end 9713.

The circuit 9730 is configured to be detectable by a control circuit of a surgical instrument to which the replaceable staple cartridge 9700 is configured to be attached. The circuit 9730 comprises circuit contacts 9731, a resistance element 9732, and electrical traces 9733 electrically coupling the contacts 9731 and the resistance element 9732. The circuit 9730 is configured to be electrically coupled with a circuit of the instrument to which the cartridge 9700 is attached upon installation of the cartridge 9700 into the instrument. The resistance element 9732 is detectable by a control circuit of the instrument. The resistance element 9732 comprises a resistance value indicative of one or more properties of the replaceable staple cartridge 9700 such as, for example, cartridge color, type, size, length, staple height, staple diameter, etc.

Upon installation of the replaceable staple cartridge 9700 into an instrument, the control circuit, such as the control circuit 9004, for example, utilizes a lookup table of resistance values to identify the one or more properties, or characteristics, of the replaceable staple cartridge 9700. Such information may also be stored in the modular electronics package. The control circuit 9004 can compare the information gathered from the circuit 9730 and the information on the modular electronics package to identify the staple cartridge 9700 and verify the authenticity of the cartridge 9700, for example. In accordance with the present disclosure, where a modular electronics package is not installed and/or not required, the control circuit 9004 can identify the cartridge 9700 using only the circuit 9730. Additionally, the circuit 9730 can be screen printed onto the cartridge body 9710.

In accordance with the present disclosure, the modular electronics package 9740, when installed in the cartridge 9700, can be electrically coupled to the circuit 9730. Such an arrangement allows the modular electronics package 9740 to identify cartridge characteristics upon installation of the modular electronics package 9740 into the replaceable staple cartridge 9700. The modular electronics package 9740 may then be configured to make adjustments to firing stroke control feedback circuits, communicate this information to a surgical instrument and/or surgical robot, for example, etc.

In accordance with the present disclosure, sensor arrays may be provided on stapling end effectors to measure one or more parameters of tissue before, during, and/or after clamping, stapling, and cutting tissue. A control circuit can be provided to intelligently decode information gathered by these sensor arrays to more accurately define a state of the tissue during a surgical stapling procedure.

Figure 23:
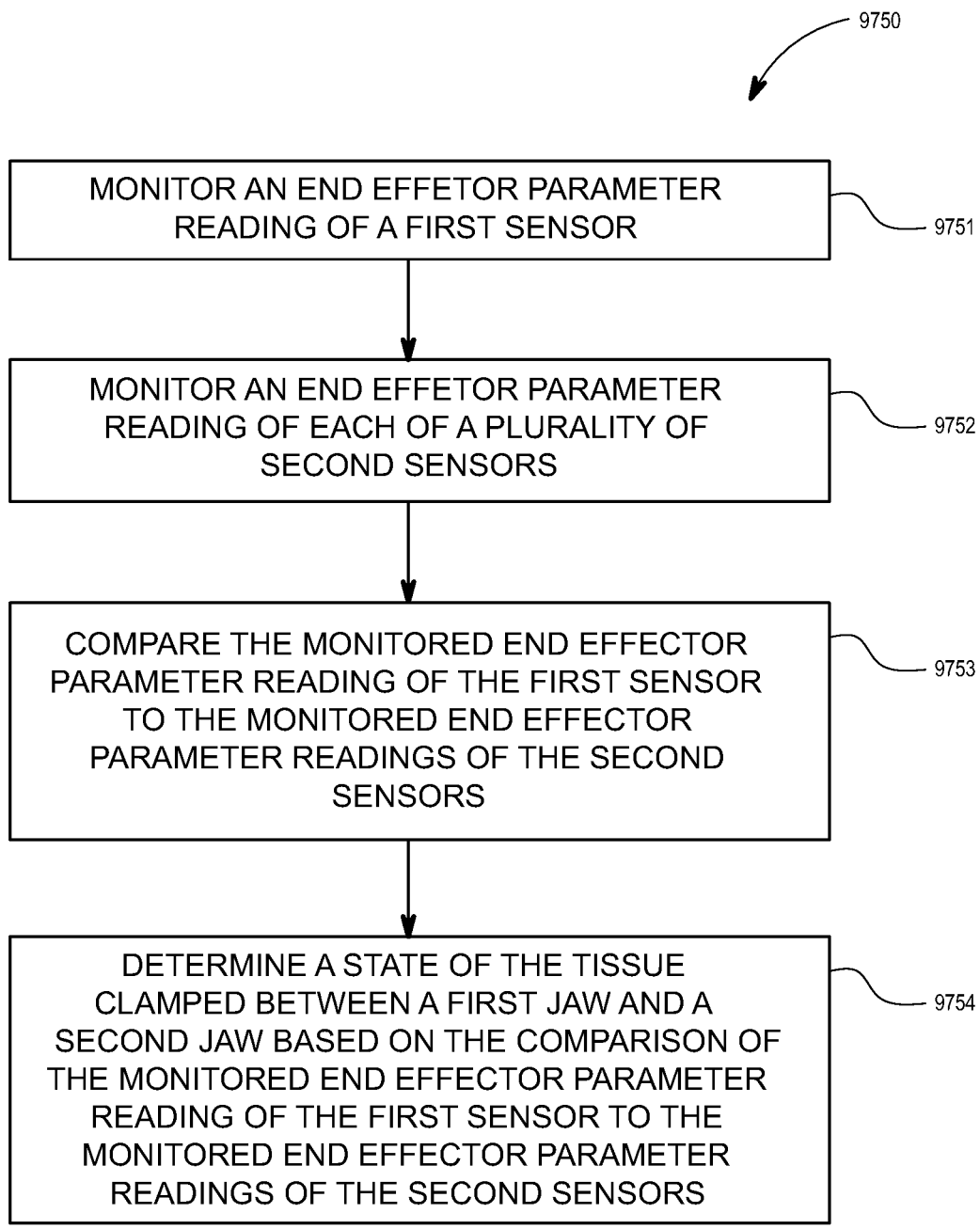
FIG. 23 is a logic flow diagram configured to be executed by a control circuit, wherein the control circuit is configured to determine a state of the tissue clamped between a first jaw and a second jaw based on a comparison of end effector parameter readings of various sensors in accordance with the present disclosure.

FIG. 23 depicts a logic flow diagram 9750 executable by a control circuit, such as the control circuit 9004, of a surgical system utilizing a sensor circuit in a stapling end effector. The steps of the control circuit can help accurately determine a state of the tissue within the stapling end effector. The control circuit is configured to monitor 9751 an end effector parameter reading of a first sensor positioned within the end effector. The control circuit is further configured to monitor 9752 an end effector parameter reading of each of a plurality of second sensors. The parameter reading may be any suitable parameter reading, such as, for example, tissue thickness, gap distance between the jaws, clamp pressure, gap distance between the tissue positioned between the jaws and one of the jaws etc. The parameter reading may be captured through any suitable sensor such as, for example, strain gauges, pressure gauges, optical sensors, capacitive sensors, distance sensors, force sensors, etc. The readings can be monitored before, during, and after tissue clamping, cutting, and stapling at a predetermined sampling rate.

The control circuit is further configured to compare 9753 the monitored end effector parameter reading of the first sensor to the monitored end effector parameter readings of the second sensors. Comparing this information allows the control circuit to analyze the readings of each of the sensors relative to each other and not in a vacuum where the end effector parameter readings of each sensor is viewed independently.

In accordance with the present disclosure, the first sensor may be distal to the plurality of second sensors, which may be distributed along a length of the stapling end effector. Positioning the first sensor distal to the plurality of the second sensors allows the control circuit to determine if the jaws of the stapling end effector have been overstuffed with tissue, for example. The control circuit can be further configured to determine 9754 a state of the tissue clamped between the first jaw and the second jaw of the stapling end effector based on the comparison of the monitored end effector parameter reading of the first sensor to the monitored end effector parameter readings of the second sensors.

In accordance with the present disclosure, the control circuit can be configured to determine if the jaws have been overstuffed or if the tissue clamped between the jaws of the stapling end effector is indeed thicker than expected, for example. If the jaws are overstuffed with tissue, the rotatable jaw to clamp the tissue may not be able to fully close, for example. Such a configuration may arise where a thick portion of tissue is stuck in the smaller gap between the jaws nearer a pivot location of the jaws. In such a configuration, a larger gap between tissue and the jaws may exist between the jaws distal to the second sensors (or nearer the distal end of the jaws, for example). In such a scenario, the plurality of second sensors may indicate that thick tissue is clamped between the jaws at the location of the second sensors. This can be determined by measuring little, to no, gap distance between the jaw on which the sensors are placed and the tissue itself, for example. Another method for determining this can include a significant pressure reading indicating the tissue is being squeezed substantially by the jaws at the location of the second sensors.

The control circuit is also configured to monitor the end effector parameter reading of the first sensor that is distal to the second sensors and compare the reading to the readings of the second sensors. In the scenario where the jaws are overstuffed (thick tissue present toward a proximal end of the jaws and thin, or no, tissue present toward the distal end), the reading of the first sensor may indicate that little, or no, tissue is present toward the distal end. This can be determined by a much greater than expected gap distance between the jaw on which the sensor is placed and the tissue itself, for example. Another method for determining this can include little, to no, pressure detected at the first sensor indicating the tissue nearer the first sensor is not substantially consuming the gap between the jaws of the stapling end effector.

In the scenario of overstuffing the jaws, a highly disproportionate difference may exist between the end effector parameter reading of the first sensor and the end effector parameter readings of the second sensors. This difference can be defined by a threshold percentage difference, for example. Once the control circuit identifies that a threshold percentage difference exists, action can be taken by the control circuit. In accordance with the present disclosure, the control circuit can be configured to alert a user that the jaws are overstuffed and/or prompt the user to unclamp, and re-clamp, tissue.

In accordance with the present disclosure, a highly disproportionate difference between the end effector parameter reading of the first sensor and the end effector parameter readings of the second sensors can indicate that the jaws are clamped onto a foreign object. In such a scenario, the control circuit may alert a user that the jaws are clamped onto a foreign object. Additionally, the control circuit can be configured to prompt a user to unclamp, and re-clamp, tissue. Highly disproportionate differences in strain values between the second sensors (an average strain across all of the second sensors) and the first sensor can indicate the presence of a foreign object.

In accordance with the present disclosure, a third sensor may be employed to measure the same, and/or a different end effector parameter. In such an instance, the control circuit can be configured to compare the highly disproportionate difference discussed above to the end effector parameter reading of the third sensor. In accordance with the present disclosure, the third sensor may comprise a Hall effect sensor. The third sensor can be used to validate, or verify, the state of tissue, or state of what is positioned between the jaws, determined when comparing the reading of the first sensor to the readings of the second sensors. A high Hall effect sensor reading can indicate an overstressed-tissue condition.

In an instance where the distal-most sensor indicates thick, or dense, tissue and the first sensor and/or second sensors indicate tissue of a nominal thickness, for example, the control circuit determines that calcified tissue and/or irregular tissue is positioned nearer the distal end of the jaws. The control circuit can then recommend not to fire with this determination of the state of the tissue.

In accordance with the present disclosure, the second sensors may comprise strain gauges positioned on the channel jaw, cartridge deck, and/or anvil jaw and the first sensor may comprise a Hall effect sensor. Additionally, one or more of the strain gauges may comprise half bridge, and/or full bridge, strain gauges. In such an instance, an electronics package module capable of receiving and decoding information gathered from the half bridge, and/or full bridge, strain gauges may be required. Any suitable strain gauge can be used. Strain gauges which measure stress and/or strain in multiple directions can allow a control circuit to determine the amount of twist experienced by the jaw to which they are attached such as, for example, anvil twist. Anvil twist is indicated by rotational twisting of the anvil relative to a longitudinal axis of the anvil.

In accordance with the present disclosure, the angle of the jaw can be measured with a first sensor, and a Hall effector sensor at the distal end can measure a gap distance between the jaws at the distal end. Additionally, a third sensor may be employed to measure tissue-conductivity in between the first sensor and the Hall effect sensor.

In accordance with the present disclosure, sensors may be selected so as to measure tissue location as well as tissue thickness. Alternatively, sensors may be selected so as to measure tissue composition. In such an instance, multiple complex sensors, which require an electronics control package with a processor to operate and use with a surgical system, such as the surgical system 9002, for example, can be utilized to measure various tissue parameters. Density, thickness, and/or electrical conductivity of the tissue are all examples of tissue parameters measurable by a complex sensor. In accordance with the present disclosure, the modular electronics package installed on the staple cartridge may comprise a multiplexer onboard the modular electronics package electrically couplable with the sensor circuits. The sensor circuits may utilize impedance spectroscopy to measure electrical properties of the tissue and/or whatever is positioned between the jaws. In accordance with the present disclosure, tissue perfusion may be measured using a sensor circuit. Additionally, multiple laser Doppler imaging sensors may be used to scan tissue.

Figure 24:
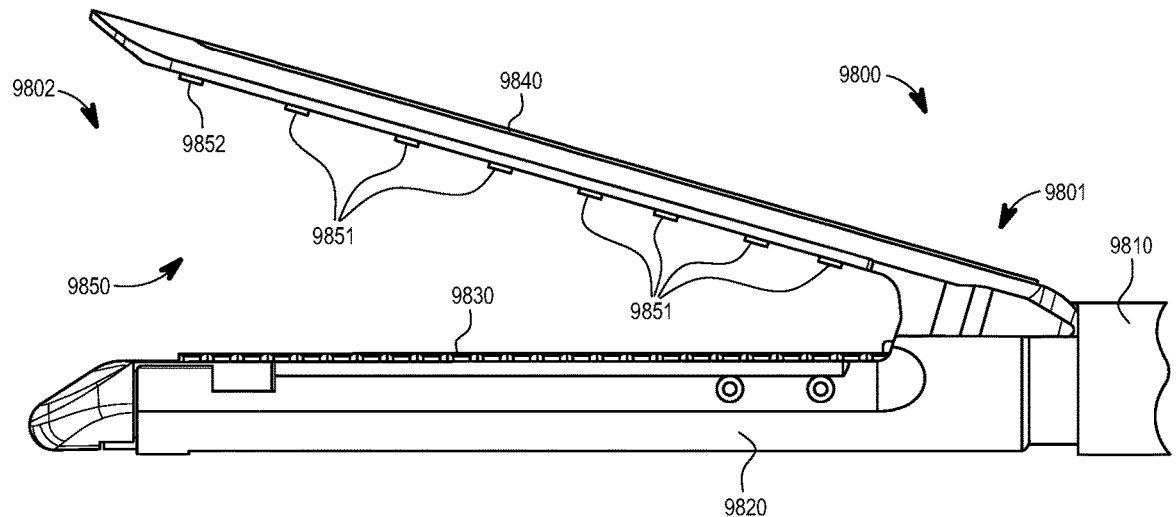
FIG. 24 is an elevational view of a surgical stapling end effector comprising a plurality of sensors, wherein the surgical stapling end effector is in an unclamped configuration in accordance with the present disclosure.
Figure 25:
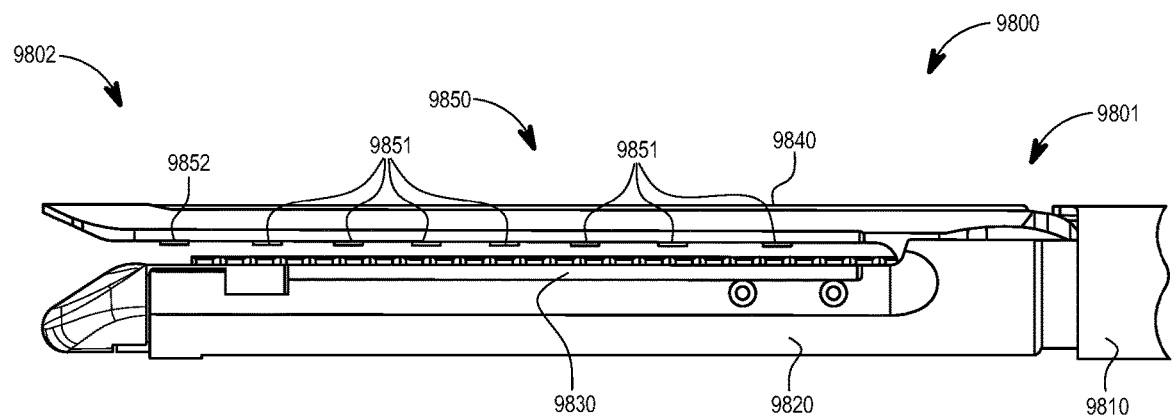
FIG. 25 is an elevational view of the surgical stapling end effector of FIG. 24, wherein the surgical stapling end effector is in a clamped configuration.
Figure 26:
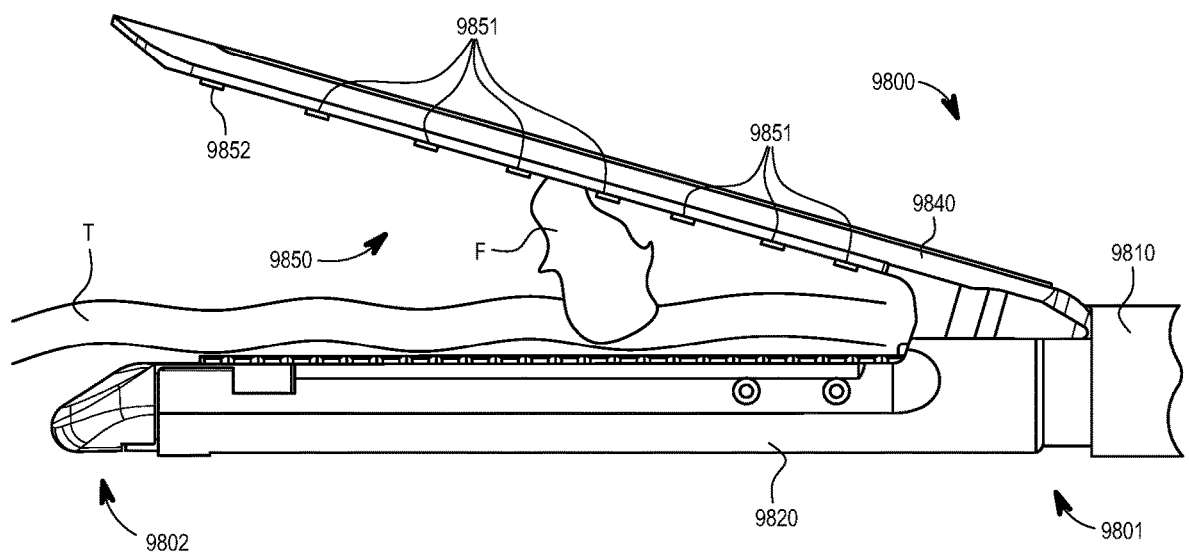
FIG. 26 is an elevational view of the surgical stapling end effector of FIG. 24, wherein the surgical stapling end effector is clamped onto a foreign object.

FIGS. 24-26 depict a surgical stapling end effector 9800. The surgical stapling end effector 9800 comprises a shaft 9810, a channel jaw 9820 configured to receive a replaceable staple cartridge 9830, and an anvil jaw 9840 movable relative to the channel jaw 9820. In accordance with the present disclosure, the channel jaw 9820 can be movable relative to the anvil jaw 9840 in addition to, or in lieu of, the anvil jaw 9840 being movable relative to the channel jaw 9820. The surgical stapling end effector 9800 comprises a sensor circuit 9850. The surgical stapling end effector 9800 can be employed with the logic flow diagram 9750 and a control circuit, such as the control circuit 9004.

The sensor circuit 9050 comprises a plurality of sensors 9851, 9852 mounted to the anvil jaw 9840. In accordance with the present disclosure, some or all of the sensors 9851, 9852 can be mounted to the channel jaw 9820 and/or the staple cartridge 9830. The plurality of sensors 9851, 9852 comprise a plurality of first sensors 9851 and a second sensor 9852 distal to the plurality of first sensors 9851. The sensors 9851, 9852 may comprise any suitable sensor to measure an end effector parameter. In accordance with the present disclosure, the sensors 9851 may comprise strain gauges to measure strain induced by clamping tissue between the jaws. Additionally, the sensor 9852 may comprise a Hall effect sensor configured to measure a gap distance between the jaws 9820, 9840 at a distal end 9802 of the surgical stapling end effector 9800. The surgical stapling end effector 9800 further comprises a proximal end 9801. FIG. 24 illustrates the jaws 9820, 9840 in an open position and FIG. 23 illustrates the jaws 9820, 9840 in a closed position.

As can be seen in FIG. 26, tissue T and a foreign object F are positioned between the jaws 9820, 9840. The fact that a foreign object F is clamped between the jaws 9820 and not thick tissue can be determined by the control circuit comparing the outputs of the sensors 9851 and the output of the sensor 9852. For example, one or more of the sensors 9851 can indicate a disproportionate gap distance measurement, for example, compared to a gap distance measurement of the sensor 9852. This disproportionate difference can indicate that a foreign object is clamped between the jaws 9820, 9840. In accordance with the present disclosure, if the jaws 9820, 9840 are over stuffed with thick tissue positioned nearer the proximal end 9801, the comparison of the outputs of the sensors 9851 and sensor 9852 can indicate a disproportionate strain difference. This disproportionate strain difference can indicate that the jaws 9820, 9840 have been overstuffed with tissue. In accordance with the present disclosure, the sensors 9851 may comprise a plurality of sensor zones monitorable by the sensors 9851 to indicate the presence of calcified, or overly thick, tissue in each zone (proximal zone, intermediate zone, and distal zone, for example). In such an instance, the control circuit can determine which zones are overstuffed with tissue, for example. In accordance with the present disclosure, an average may be taken of the outputs of each sensor 9851, or each zone of sensors 9851, and the average can be compared to the output of the sensor 9852.

In accordance with the present disclosure, electrical traces can be positioned within one or more pathways, or channels, defined in and/or on the anvil jaw and/or the staple cartridge jaw and can be coupled with sensors along the length of the anvil jaw and/or staple cartridge jaw. Additionally, the pathways can be cut into the jaws with a laser. Alternatively, the electrical traces can be plated onto the jaws.

In accordance with the present disclosure, a wireless coil may be first used to check cartridge viability (authenticity, unfired, etc.) and, upon passing a first check through the wireless coil, the control circuit can be configured permit power and/or data transfer to the staple cartridge assembly through another coil and/or other electrical system (hardwired, electrical connector, etc.).

Figure 27:
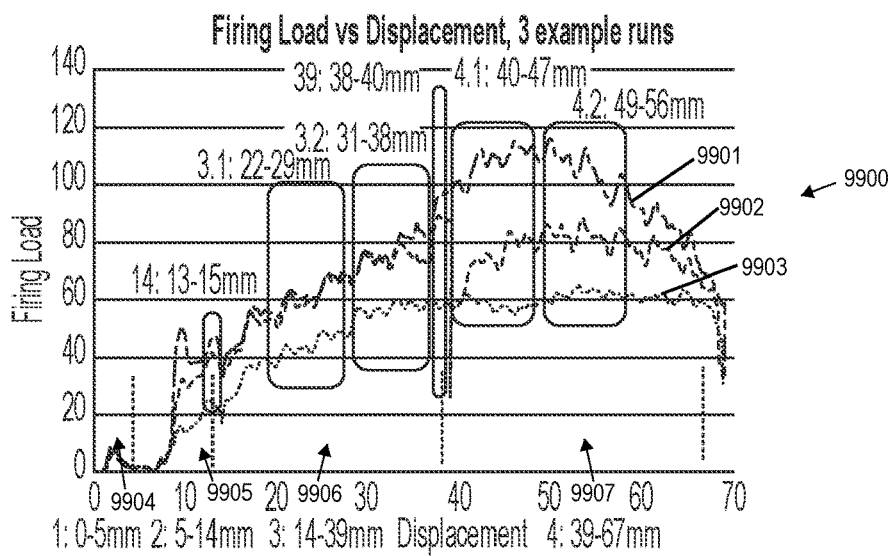
FIG. 27 is a graph of multiple firing strokes of a stapling end effector including multiple discrete sensor zones.

FIG. 27 is a graph 9900 of three firing strokes 9901, 9902, 9903 where an end effector contains multiple sensor zones 9904, 9905, 9906, 9907. Each sensor zone 9904, 9905, 9906, 9907 contains at least one sensor such as, for example, a strain gauge, configured to sense a parameter of the firing stroke (tissue thickness, tissue toughness, firing driver speed, tissue clamping pressure, etc.) within the corresponding sensor zone. Having sensors within discrete zones of the end effector can allow for more targeted measurements of tissue based on predictable behavior of the end effector within each zone. As a result, unpredictable sensor readings would indicate an abnormal condition such as, for example, over stuffing of the jaws.

For example, nearer the distal end of a stapling end effector, the cantilever beam effect of the jaw which is clamped from an open position to a closed position can be higher than the cantilever beam effector of the jaw nearer the proximal end of the stapling end effector. This cantilever beam effect can result in greater strain value measurements within these zones given the jaw's inability to resist deflection in this zone compared to more proximal zones where the movable jaw is much stiffer. A higher strain reading within this distal zone, for example, could be expected given the decreased stiffness of the jaw within this zone compared to others. This sensor reading can be compared to different sensor reading thresholds as compared to other zones given the difference in predictable behavior of the zone. Similarly, nearer the proximal end of the stapling end effector, the movable jaw may comprise a much greater stiffness and not be expected to experience the same amount of strain as more distal zones under a given tissue load. Thus, a predetermined tissue-overstuffing strain value indicative of tissue over-stuffing may be much lower in this zone as compared to a more distal zone. Given the greater stiffness of this portion of the movable jaw, the same amount increase, for example, of the measured strain value relative to the predetermined tissue-overstuffing strain value in both zones with different jaw stiffness, for example, may indicate a much more significant overstuffing scenario in the zone where the movable jaw is much stiffer. Placing sensors in discrete zones can allow a control circuit to determine which zone is experiencing overstuffing, for example.

Figure 29:
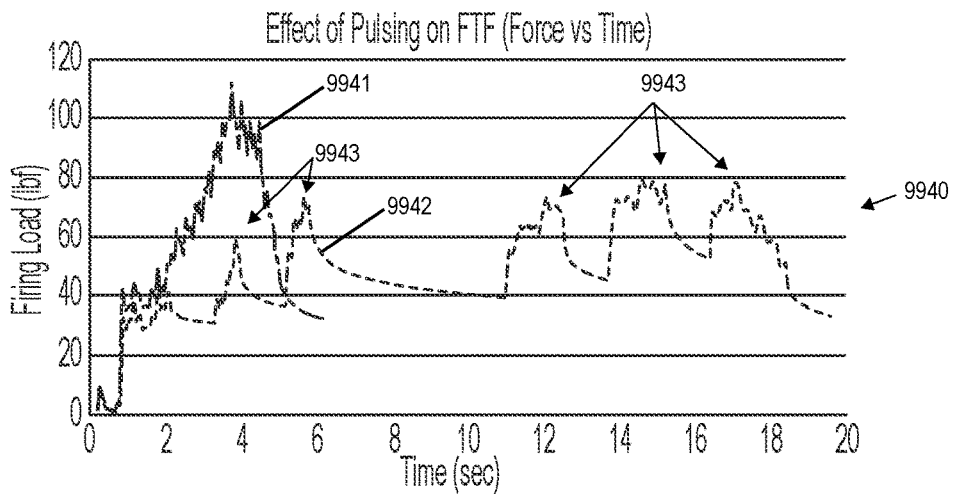
FIG. 29 is a graph of multiple firing strokes of a stapling end effector where one of the firing strokes is pulsed to alleviate firing load.
Figure 28:
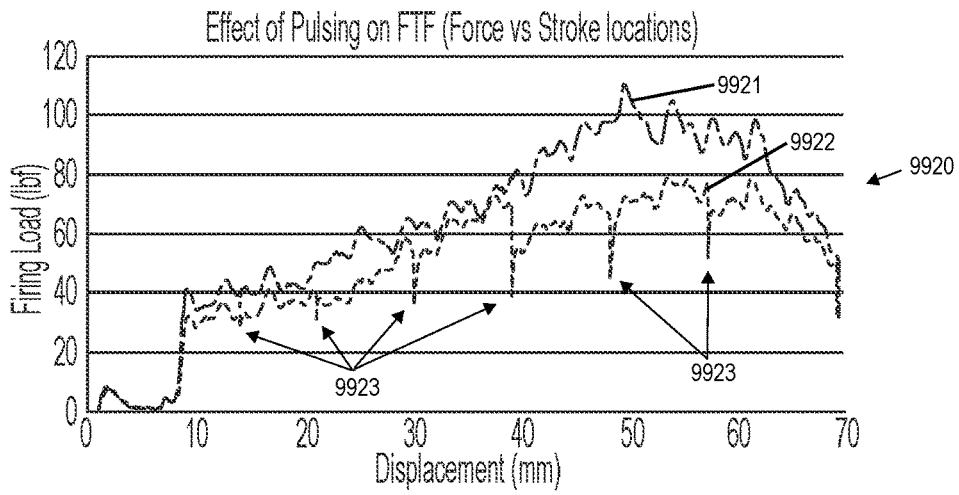
FIG. 28 is a graph of multiple firing strokes of a stapling end effector where one of the firing strokes is pulsed to alleviate firing load.

FIGS. 28 and 29 illustrate the effects of pulsing a firing stroke relative to not pulsing a firing stroke of a stapling end effector. FIG. 28 is a graph 9920 of a first firing stroke 9921 and a second firing stroke 9922 of a stapling end effector plotting firing load (y axis) vs displacement (x axis). The difference between the strokes 9921, 9923 is that the second firing stroke 9922 includes a pulsed firing stroke where a firing motor is pulsed throughout the firing stroke to reduce firing load throughout the firing stroke. As can be seen in the graph 9920, the second firing stroke experiences, on average, less firing load over the duration of the firing stroke given the pulses 9923. Pulsing the firing motor in such a fashion can allow the tissue to relax, or soften, briefly so as to lighten the firing load on a cutting edge of a firing driver, for example. FIG. 29 is a graph 9940 of a first firing stroke 9941 and a second firing stroke 9942 where the second firing stroke 9942 is pulsed throughout the duration of the firing stroke 9942. As can be seen in the graph 9940, the firing load is maintained below a threshold throughout the duration of the second firing stroke 9942 at least because of the pulsing 9943 of the firing motor, for example.

Various aspects of the subject matter described herein are set out in the following examples:

Example 1—A surgical stapling end effector (9010, 9100, 9200) comprising a cartridge channel jaw (9220), an anvil jaw (9230), and a surgical staple cartridge (9240) positioned within the cartridge channel jaw. The surgical staple cartridge comprises a plurality of staples (9101), a cartridge body (9241) comprising a plurality of staple cavities (9242), a longitudinal slot (9243), and an outer lateral cartridge wall (9244) comprising a recess (9245) defined therein, and an electronics sub-assembly (9250) positioned within the recess. The electronics sub-assembly comprises electrical pathways (9280), a printed circuit board (9260) removably attached to the outer lateral cartridge wall within the recess, and a wireless transmission coil (9270) electrically coupled to the printed circuit board by way of the electrical pathways, wherein the wireless transmission coil is configured to transmit at least one of power or data between the printed circuit board and a corresponding wireless transmission coil (9290) of an instrument to which the surgical staple cartridge is attached.

Example 2—The surgical stapling end effector of Example 1, wherein the wireless transmission coil comprises a proximal wireless transmission coil (9271) and a distal wireless transmission coil (9272).

Example 3—The surgical stapling end effector of Examples 1 or 2, further comprising a resistance circuit (9730) positioned on a proximal end of the outer lateral cartridge wall, and wherein the resistance circuit is detectable by the instrument to which the surgical staple cartridge is attached, and wherein the resistance circuit comprises a predetermined resistance indicative of a cartridge characteristic of the surgical staple cartridge.

Example 4—The surgical stapling end effector of Example 3, wherein the resistance circuit comprises a resistive leg (9732) and a pair of electrical contacts (9731) in electrical communication with the resistive leg, wherein corresponding electrical contacts of the instrument to which the surgical staple cartridge is attached are configured to contact the pair of electrical contacts to determine the resistance of the resistance circuit.

Example 5—The surgical stapling end effector of Examples 3 or 4, wherein the resistance circuit is positioned proximal to the staple cavities.

Example 6—The surgical stapling end effector of Examples 1, 2, 3, 4, or 5, further comprising an electrical connector (9370) extending from a proximal end (9341) of the surgical staple cartridge, wherein the electrical connector is in electrical communication with the printed circuit board, and wherein the electrical connector is configured to be coupled to a corresponding electrical connector (9360) of the instrument to which the surgical staple cartridge is attached.

Example 7—The surgical stapling end effector of Examples 1, 2, 3, 4, 5, or 6, wherein the printed circuit board further comprises a processor and a memory.

Example 8—The surgical stapling end effector of Examples 1, 2, 3, 4, 5, 6, or 7, wherein the wireless transmission coil comprises a first wireless transmission coil (9270), wherein the cartridge channel jaw comprises a flex circuit and a second wireless transmission coil (9290) mounted to a sidewall (9221) of the cartridge channel jaw.

Example 9—The surgical stapling end effector of Example 8, wherein the cartridge channel jaw comprises a slot (9223) defined in a cartridge-supporting surface of the cartridge channel jaw, and wherein the flex circuit is positioned within the slot.

Example 10—A surgical stapling system (9010, 9100, 9200, 9800) comprising a surgical end effector (9800) comprising a first jaw (9820), a second jaw movable (9840) relative to the first jaw, a plurality of sensors (9851, 9852) arranged longitudinally along the surgical end effector, wherein each sensor of the plurality of sensors is configured to sense a parameter of tissue clamped between the first jaw and the second jaw, and wherein the plurality of sensors comprises a first sensor (9852) and a plurality of second sensors (9851) proximal to the first sensor, and a control circuit (9004, 9750) coupled to the plurality of sensors, wherein the control circuit is configured to monitor (9751) an end effector parameter reading of the first sensor, monitor (9752) an end effector parameter reading of each sensor of the plurality of second sensors, compare (9753) the end effector parameter reading of the first sensor to the end effector parameter readings of the plurality of second sensors, and determine (9754) a state of the tissue clamped between the first jaw and the second jaw based on the comparison of the end effector parameter reading of the first sensor and the end effector parameter readings of the plurality of second sensors.

Example 11—The surgical stapling system of Example 10, wherein the end effector parameter reading comprises a gap distance between one of the first jaw and the second jaw and the tissue.

Example 12—The surgical stapling system of Example 11, wherein each sensor of the plurality of sensors comprises a Hall effect sensor.

Example 13—The surgical stapling system of Claims 10, 11, or 12, wherein the end effector parameter reading comprises a tissue-clamping pressure.

Example 14—The surgical stapling system of Claim 13, wherein each sensor of the plurality of sensors comprises a strain gauge.

Example 15—The surgical stapling system of Claims 10, 11, 12, 13, or 14, wherein the first sensor is distal to the second sensors.

Example 16—A surgical stapling end effector comprising a cartridge channel jaw, an anvil jaw, and a surgical staple cartridge positioned within the cartridge channel jaw. The surgical staple cartridge comprises a plurality of staples, a cartridge body comprising a plurality of staple cavities, a longitudinal slot, and an outer lateral cartridge wall comprising a recess defined therein. The surgical staple cartridge further comprises an electronics sub-assembly positioned within the recess, wherein the electronics sub-assembly comprises electrical pathways, a printed circuit board removably attached to the outer lateral cartridge wall within the recess, and a wireless transmission coil electrically coupled to the printed circuit board by way of the electrical pathways, wherein the wireless transmission coil is configured to transmit at least one of power or data between the printed circuit board and a corresponding wireless transmission coil of an instrument to which the surgical staple cartridge is attached.

Example 17—The surgical stapling end effector of Example 16, wherein the wireless transmission coil comprises a proximal wireless transmission coil and a distal wireless transmission coil.

Example 18—The surgical stapling end effector of Examples 16 or 17, further comprising a resistance circuit positioned on a proximal end of the outer lateral cartridge wall, and wherein the resistance circuit is detectable by the instrument to which the surgical staple cartridge is attached, and wherein the resistance circuit comprises a predetermined resistance indicative of a cartridge characteristic of the surgical staple cartridge.

Example 19—The surgical stapling end effector of Examples 16, 17, or 18, wherein the resistance circuit comprises a resistive leg, and a pair of electrical contacts in electrical communication with the resistive leg, wherein corresponding electrical contacts of the instrument to which the surgical staple cartridge is attached are configured to contact the pair of electrical contacts to determine the resistance of the resistance circuit.

Example 20—The surgical stapling end effector of Examples 16, 17, 18, or 19, wherein the resistance circuit is positioned proximal to the staple cavities.

Example 21—The surgical stapling end effector of Examples 16, 17, 18, or 19, further comprising an electrical connector extending from a proximal end of the surgical staple cartridge, wherein the electrical connector is in electrical communication with the printed circuit board, and wherein the electrical connector is configured to be coupled to a corresponding electrical connector (9360) of the instrument to which the surgical staple cartridge is attached.

Example 22—The surgical stapling end effector of Examples 16, 17, 18, 19, 20, or 21, wherein the printed circuit board further comprises a processor and a memory.

Example 23—The surgical stapling end effector of Examples 16, 17, 18, 19, 20, or 21, wherein the wireless transmission coil comprises a first wireless transmission coil, wherein the cartridge channel jaw comprises a flex circuit and a second wireless transmission coil mounted to a sidewall of the cartridge channel jaw.

Example 24—The surgical stapling end effector of Examples 16, 17, 18, 19, 20, 21, 22, or 23, wherein the cartridge channel jaw comprises a slot defined in a cartridge-supporting surface of the cartridge channel jaw, and wherein the flex circuit is positioned within the slot.

Example 25—A surgical stapling system comprising a surgical end effector comprising a first jaw, a second jaw movable relative to the first jaw, and a plurality of sensors arranged longitudinally along the surgical end effector, wherein each sensor of the plurality of sensors is configured to sense a parameter of tissue clamped between the first jaw and the second jaw, and wherein the plurality of sensors comprises a first sensor and a plurality of second sensors proximal to the first sensor. The surgical stapling system further comprises a control circuit coupled to the plurality of sensors, wherein the control circuit is configured to monitor an end effector parameter reading of the first sensor, monitor an end effector parameter reading of each sensor of the plurality of second sensors, compare the end effector parameter reading of the first sensor to the end effector parameter readings of the plurality of second sensors, and determine a state of the tissue clamped between the first jaw and the second jaw based on the comparison of the end effector parameter reading of the first sensor and the end effector parameter readings of the plurality of second sensors.

Example 26—The surgical stapling system of Example 25, wherein the end effector parameter reading comprises a gap distance between one of the first jaw and the second jaw and the tissue.

Example 27—The surgical stapling system of Examples 25 or 26, wherein each sensor of the plurality of sensors comprises a Hall effect sensor.

Example 28—The surgical stapling system of Examples 25, 26, or 27, wherein the end effector parameter reading comprises a tissue-clamping pressure.

Example 29—The surgical stapling system of Examples 25, 26, 27, or 28, wherein each sensor of the plurality of sensors comprises a strain gauge.

Example 30—The surgical stapling system of Examples 25, 26, 27, 28, or 29, wherein the first sensor is distal to the second sensors.

Example 31—The surgical stapling system of Examples 25, 26, 27, 28, 29, or 30, wherein the first sensor comprises a Hall effect sensor and the plurality of second sensors comprise strain gauges.

Example 32—A surgical staple cartridge configured to be installed into a cartridge channel jaw of a stapling end effector, wherein the surgical staple cartridge comprises a plurality of staples and a cartridge body comprising a plurality of staple cavities, a longitudinal slot, and outer cartridge sidewalls, wherein one of the outer cartridge sidewalls comprises a recess defined therein extending longitudinally along the one of the outer cartridge sidewalls, and wherein the recess comprises a proximal portion and a distal portion. The surgical staple cartridge further comprises an electronics sub-assembly positioned within the recess, wherein the electronics sub-assembly comprises electrical traces extending between the proximal portion and the distal portion, a printed circuit board configured to be installed in the distal portion of the recess, and a wireless transmission coil electrically coupled to the printed circuit board by way of the electrical traces, wherein the wireless transmission coil is positioned within the proximal portion of the recess and is configured to transmit at least one of power or data between the printed circuit board and a corresponding wireless transmission coil of the stapling end effector within which the surgical staple cartridge is configured to be installed.

Example 33—The surgical staple cartridge of Example 32, wherein the wireless transmission coil comprises a proximal wireless transmission coil and a distal wireless transmission coil.

Example 34—The surgical staple cartridge of Examples 32 or 33, further comprising a resistance circuit positioned on a proximal end of the one of the outer cartridge sidewalls, and wherein the resistance circuit is detectable, and wherein the resistance circuit comprises a predetermined resistance indicative of a cartridge characteristic of the surgical staple cartridge.

Many of the surgical instrument systems described herein are motivated by an electric motor; however, the surgical instrument systems described herein can be motivated in any suitable manner. In accordance with the present disclosure, the surgical instrument systems described herein can be motivated by a manually-operated trigger, for example. Additionally, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. According to various embodiments, a single component may be replaced by multiple components, and multiple components may be replaced by a single component, to perform a given function or functions. The foregoing description and following claims are intended to cover all such modification and variations.

While several configurations have been described, additional modifications are within the scope of the present disclosure, which is intended to cover any variations, uses, or adaptations of the disclosed configurations using its general principles.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. The instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" or "control system" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in one aspect. Thus, appearances of the phrases "in one aspect," "in an aspect," "in an exemplification," and "in one exemplification" in various places throughout the specification are not necessarily all referring to the same aspect. The particular features, structures or characteristics may be combined in any suitable manner in various aspects.

It is worthy to note that any reference numbers included in the appended claims are used to reference exemplary embodiments/elements described in the present disclosure. Accordingly, any such reference numbers are not meant to limit the scope of the subject matter recited in the appended claims.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A surgical stapling end effector, comprising:
 a cartridge channel jaw;
 an anvil jaw; and
 a surgical staple cartridge positioned within the cartridge channel jaw, wherein the surgical staple cartridge comprises:
  a plurality of staples;
  a cartridge body, comprising:
   a plurality of staple cavities;
   a longitudinal slot; and
   an outer lateral cartridge wall comprising a recess defined therein; and
  an electronics sub-assembly positioned within the recess, wherein the electronics sub-assembly comprises:
   electrical pathways;
   a printed circuit board removably attached to the outer lateral cartridge wall within the recess; and a wireless transmission coil electrically coupled to the printed circuit board by way of the electrical pathways, wherein the wireless transmission coil is configured to transmit at least one of power or data between the printed circuit board and a corresponding wireless transmission coil of an instrument to which the surgical staple cartridge is attached.

2. The surgical stapling end effector of claim 1, wherein the wireless transmission coil comprises a proximal wireless transmission coil and a distal wireless transmission coil.

3. The surgical stapling end effector of claim 1, further comprising a resistance circuit positioned on a proximal end of the outer lateral cartridge wall, and wherein the resistance circuit is detectable by the instrument to which the surgical staple cartridge is attached, and wherein the resistance circuit comprises a predetermined resistance indicative of a cartridge characteristic of the surgical staple cartridge.

4. The surgical stapling end effector of claim 3, wherein the resistance circuit comprises:
  a resistive leg; and
  a pair of electrical contacts in electrical communication with the resistive leg, wherein corresponding electrical contacts of the instrument to which the surgical staple cartridge is attached are configured to contact the pair of electrical contacts to determine the resistance of the resistance circuit.

5. The surgical stapling end effector of claim 4, wherein the resistance circuit is positioned proximal to the staple cavities.

6. The surgical stapling end effector of claim 1, further comprising an electrical connector extending from a proximal end of the surgical staple cartridge, wherein the electrical connector is in electrical communication with the printed circuit board, and wherein the electrical connector is configured to be coupled to a corresponding electrical connector (9360) of the instrument to which the surgical staple cartridge is attached.

7. The surgical stapling end effector of claim 1, wherein the printed circuit board further comprises a processor and a memory.

8. The surgical stapling end effector of claim 1, wherein the wireless transmission coil comprises a first wireless transmission coil, wherein the cartridge channel jaw comprises a flex circuit and a second wireless transmission coil mounted to a sidewall of the cartridge channel jaw.

9. The surgical stapling end effector of claim 8, wherein the cartridge channel jaw comprises a slot defined in a cartridge-supporting surface of the cartridge channel jaw, and wherein the flex circuit is positioned within the slot.

10. A surgical stapling system, comprising:
  a surgical end effector, comprising:
    a first jaw;
    a second jaw movable relative to the first jaw;
    a plurality of sensors arranged longitudinally along the surgical end effector, wherein each sensor of the plurality of sensors is configured to sense a parameter of tissue clamped between the first jaw and the second jaw, and wherein the plurality of sensors comprises a first sensor and a plurality of second sensors proximal to the first sensor; and
  a control circuit coupled to the plurality of sensors, wherein the control circuit is configured to:
    monitor an end effector parameter reading of the first sensor;
    monitor an end effector parameter reading of each sensor of the plurality of second sensors;
    compare the end effector parameter reading of the first sensor to the end effector parameter readings of the plurality of second sensors;
    determine a state of the tissue clamped between the first jaw and the second jaw based on the comparison of the end effector parameter reading of the first sensor and the end effector parameter readings of the plurality of second sensors.

11. The surgical stapling system of claim 10, wherein the end effector parameter reading comprises a gap distance between one of the first jaw and the second jaw and the tissue.

12. The surgical stapling system of claim 11, wherein each sensor of the plurality of sensors comprises a Hall effect sensor.

13. The surgical stapling system of claim 10, wherein the end effector parameter reading comprises a tissue-clamping pressure.

14. The surgical stapling system of claim 13, wherein each sensor of the plurality of sensors comprises a strain gauge.

15. The surgical stapling system of claim 10, wherein the first sensor is distal to the second sensors.

16. The surgical stapling system of claim 15, wherein the first sensor comprises a Hall effect sensor and the plurality of second sensors comprise strain gauges.

17. A surgical staple cartridge configured to be installed into a cartridge channel jaw of a stapling end effector, wherein the surgical staple cartridge comprises:
  a plurality of staples;
  a cartridge body, comprising:
    a plurality of staple cavities;
    a longitudinal slot; and
    outer cartridge sidewalls, wherein one of the outer cartridge sidewalls comprises a recess defined therein extending longitudinally along the one of the outer cartridge sidewalls, and wherein the recess comprises a proximal portion and a distal portion; and
  an electronics sub-assembly positioned within the recess, wherein the electronics sub-assembly comprises:
    electrical traces extending between the proximal portion and the distal portion;
    a printed circuit board configured to be installed in the distal portion of the recess; and
    a wireless transmission coil electrically coupled to the printed circuit board by way of the electrical traces, wherein the wireless transmission coil is positioned within the proximal portion of the recess and is configured to transmit at least one of power or data between the printed circuit board and a corresponding wireless transmission coil of the stapling end effector within which the surgical staple cartridge is configured to be installed.

18. The surgical staple cartridge of claim 17, wherein the wireless transmission coil comprises a proximal wireless transmission coil and a distal wireless transmission coil.

19. The surgical staple cartridge of claim 17, further comprising a resistance circuit positioned on a proximal end of the one of the outer cartridge sidewalls, and wherein the resistance circuit is detectable, and wherein the resistance circuit comprises a predetermined resistance indicative of a cartridge characteristic of the surgical staple cartridge.

* * * * *